United States Patent [19]
Ogata et al.

[11] Patent Number: 5,110,825
[45] Date of Patent: May 5, 1992

[54] BENZOFURAN DERIVATIVE

[75] Inventors: Masaru Ogata, Hyogo; Hiroshi Matsumoto, Osaka; Sumio Shimizu, Hyogo; Shiro Kida, Osaka, all of Japan

[73] Assignee: Shionogi & Co., Ltd., Osaka, Japan

[21] Appl. No.: 623,614

[22] Filed: Dec. 7, 1990

[30] Foreign Application Priority Data

Dec. 28, 1989 [JP] Japan .................. 1-342757

[51] Int. Cl.$^5$ .............. A01N 43/64; C07D 307/78
[52] U.S. Cl. ........................... 514/381; 514/382; 514/451; 514/459; 514/460; 514/469; 514/470; 548/250; 548/252; 548/253; 548/254; 549/414; 549/467; 549/469; 549/471; 549/292; 549/462
[58] Field of Search ............... 549/292, 462, 414, 467, 549/469, 471; 548/252, 250, 253, 254; 514/470, 382, 469, 381, 451, 459, 460

[56] References Cited

U.S. PATENT DOCUMENTS

| | | | |
|---|---|---|---|
| 4,260,776 | 4/1981 | Harnisch | 549/292 |
| 4,444,784 | 4/1984 | Hoffman et al. | 424/279 |
| 4,816,473 | 3/1989 | Dunn | 549/462 |
| 4,927,851 | 5/1990 | Damon, II et al. | 549/292 |

FOREIGN PATENT DOCUMENTS 59-48418 3/1984 Japan .

OTHER PUBLICATIONS

Derwent Abstract of Japanese Patent Publication No. 59-48418.
Alberts et al., Proc. Natl. Acad. Sci. USA, vol. 77, No. 7, pp. 3957-3961, Jul. 1980.

Primary Examiner—C. Warren Ivy
Assistant Examiner—Raymond Covington
Attorney, Agent, or Firm—Wenderoth, Lind & Ponack

[57] ABSTRACT

The compounds of the present invention inhibit HMG-CoA reductase, subsequently suppress the synthesis of cholesterol; and are useful in the treatment of hypercholesterolemia, hyperlipoproteinemia, and atherosclerosis.

4 Claims, No Drawings

BENZOFURAN DERIVATIVE

BACKGROUND OF THE INVENTION

1. Field of the Invention

The present invention relates to 3-hydroxy-3-methylglutaryl coenzyme A (HMG-CoA) reductase inhibitor.

2. Prior Art

Mevinolin (Proc. Natl. Acad. Sci. U.S.A., 77, 3957 (1980)), pravastatin (JP Unexamd. Pat. Publn. No. 59-48418), and simvastatin (U.S. Pat. No. 4,444,784) are known as drugs for the treatment of atherosclerosis by inhibiting the activity of HMG-CoA reductase.

SUMMARY OF THE INVENTION

This invention relates to 3-hydroxy-3-methylglutaryl coenzyme A (HMG-CoA) reductase inhibitor. Furthermore, the compounds of this invention inhibit the HMG-CoA reductase which plays a main role in the synthesis of cholesterol, and subsequently they suppress the synthesis of cholesterol. Therefore, they are useful in the treatment of hypercholesterolemia, hyperlipoproteinemia, and atherosclerosis.

DETAILED DESCRIPTION

The present invention relates to compounds of the formula:

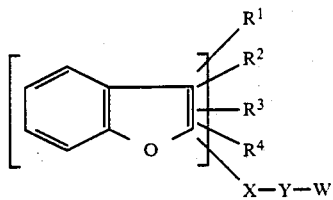

wherein $R^1$, $R^2$, $R^3$, and $R^4$ each is hydrogen, halogen, cyano, lower alkanoyl, optionally substituted lower alkyl, optionally substituted amino, optionally substituted phenyl, or optionally substituted carboxy; X-Y is $-CZ^7=CZ^1-$ or $-CZ^7-CHZ^2-$; W is

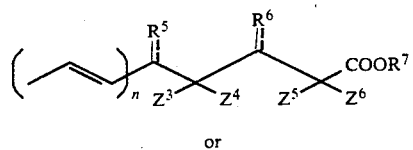

or

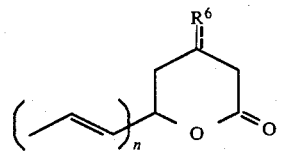

wherein $R^5$ and $R^6$ each is hydroxy or oxo; $R^7$ is hydrogen, lower alkyl, quaternary ammonium, alkali metal, or alkaline earth metal; $Z^1$, $Z^2$, and $Z^7$ each is hydrogen, optionally substituted phenyl, or optionally substituted tetrazole; $Z^3$, $Z^4$, $Z^5$, and $Z^6$ each is hydrogen or halogen; n is an integer of 0 or 1; the dotted line represents the presence or absence of a double bond; $R^1$, $R^2$, $R^3$, $R^4$, and X-Y-W each may be attached to either the benzene ring or furan ring.

In this specification, the term "lower alkyl" refers to a straight or branched chain $C_1$ to $C_6$ alkyl, including methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl, neohexyl, 2-methylpentyl, 3-methylpentyl and the like. Further these lower alkyls may be optionally substituted by halogen, lower alkoxy, and cyano.

The term "lower alkanoyl" refers to $C_1$ to $C_4$ alkanoyl including formyl, acetyl, propionyl, butyryl, or isobutyryl.

The term "optionally substituted carboxy" refers to ester or amide.

The term "optionally substituted amino" refers to substituted or unsubstituted amino. Examples of the substituents are lower alkyl, lower alkoxy, and ester.

The term "optionally substituted phenyl" refers to substituted or unsubstituted phenyl. Examples of the substituents are lower alkyl, lower alkoxy, and halogen.

The term "optionally substituted tetrazole" refers to substituted or unsubstituted tetrazole. Examples of the substituents are lower alkyl, lower alkoxy, and halogen.

The term "alkali metal" refers to lithium, sodium, potassium, and cesium.

The term "alkaline earth metal" refers to calcium, strontium, barium, beryllium, and magnesium.

The term "quaternary ammonium" refers to tetraalkylamino such as tetramethylamino, and alkyl pyridium such as methylpyridium.

The term "lower alkoxy" refers to methoxy, ethoxy, butoxy, and propoxy.

The compounds of this invention can be prepared by the following method.

METHOD A

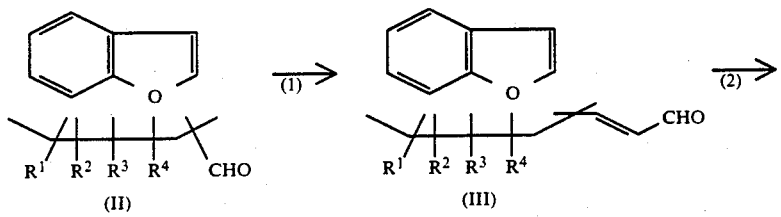

METHOD A
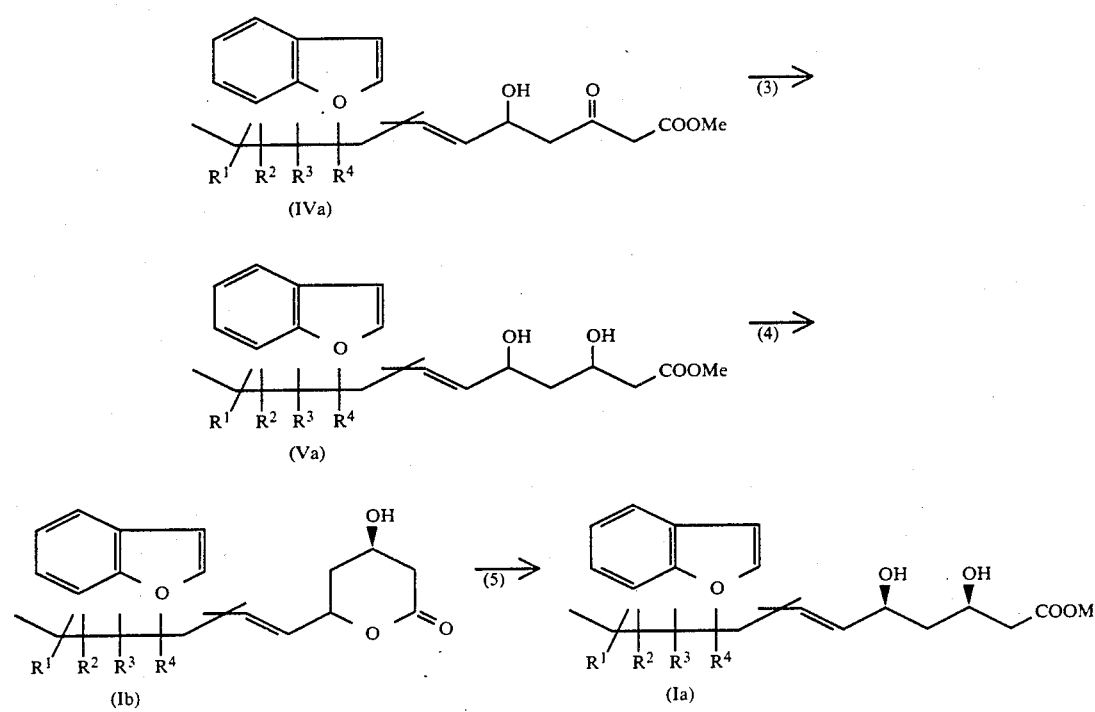
METHOD B
(II) →(1)→ (III) →(2)→ (IVa) →(3)→
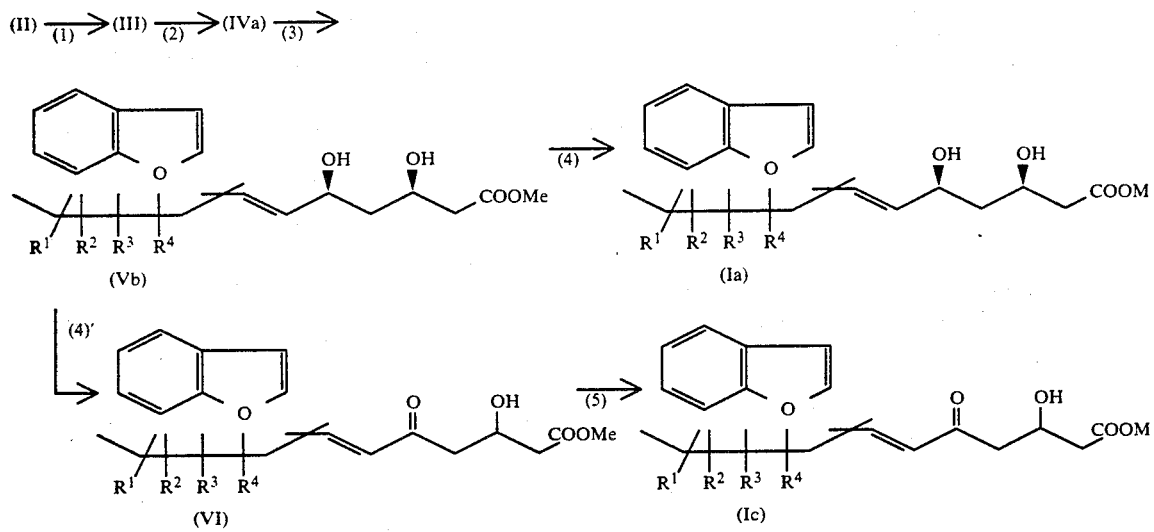
METHOD C
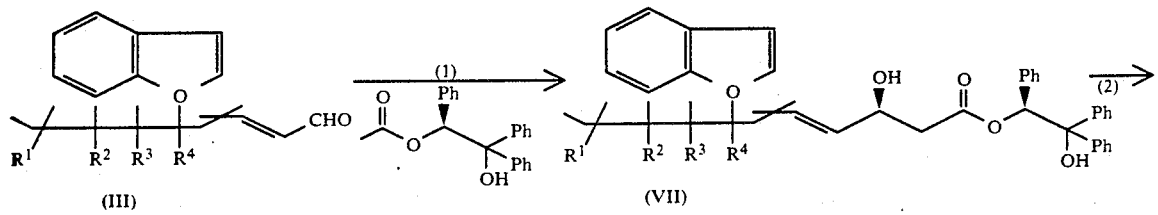

-continued
METHOD C
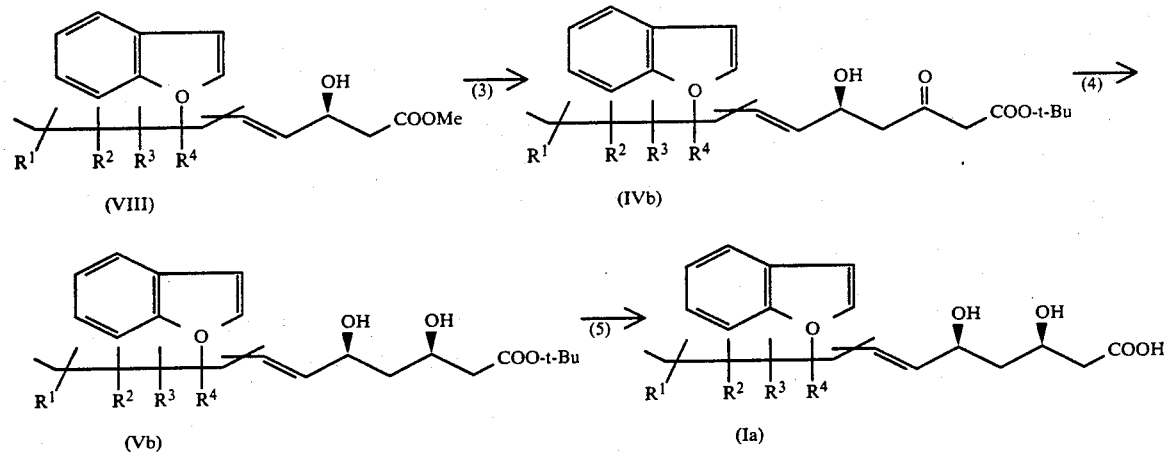
METHOD D
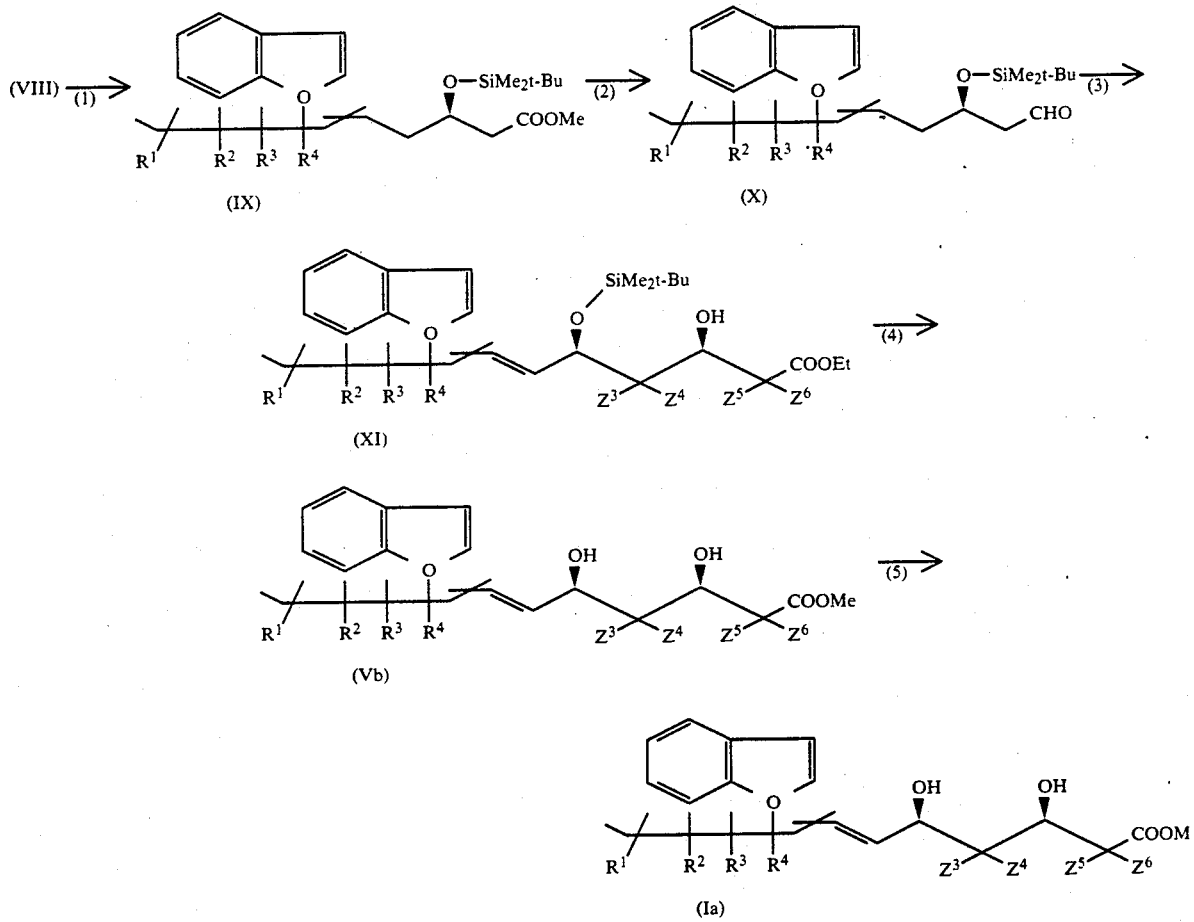
METHOD E
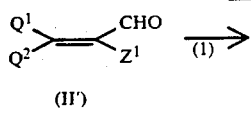
-continued
METHOD E
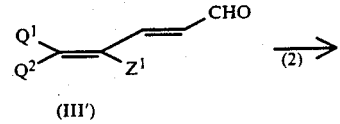

-continued
METHOD E

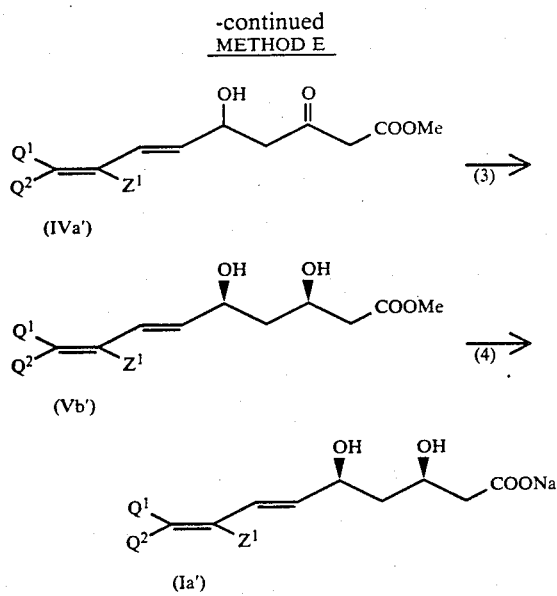

Wherein $R^1$, $R^2$, $R^3$, $R^4$, $Z^3$, $Z^4$, $Z^5$, and $Z^6$ each has the same meaning defined above, and M means alkali metal or alkaline earth metal; $Q^1$ and $Q^2$ each is

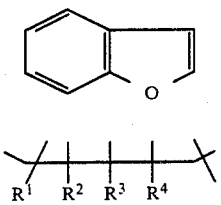

or $Z^7$, and they are not identity each other.

METHOD A

Step 1

The compound (III) can be prepared by the reaction of formyl compound (II) with [2-(1,3-dioxane-2-yl)methyl]triphenylphosphoniumbromide in an organic solvent, preferably under heating.

The reaction is performed at a temperature in the range of from 0° to 200° C., preferably from room temperature to 120° C., for about 10 minutes to about 20 hours, preferably about 30 minutes to about 8 hours. An organic solvent which may be used are alcohols such as methanol and ethanol, ethers such as diethyl-ether and tetrahydrofuran, dimethylformamide, acetonitrile and the like, most preferably dimethylformamide.

Step 2

The compound (III) is dissolved in an organic solvent preferably under nitrogen atmosphere and is added dropwise to a dianionic methyl acetoacetate solution (normally, obtained by reaction with sodium hydride and then butyllithium in THF) to give the compound (IVa).

The reaction is performed at a temperature under cooling in the range of from −80° to 0° C., for about 5 minutes to about 3 hours, preferably about 15 minutes to about 1 hour. An organic solvent as mentioned in the above step 1 may be used, most preferably tetrahydrofuran.

Step 3

The compound (IVa) is dissolved in an alcoholic solvent, and the solution is reacted with $NaBH_4$ to prepare the compound (Va).

The reaction is performed at a temperature under cooling for about 5 minutes to about 1 hour, preferably for about 15 to about 30 minutes. As alcohol which may be used are methanol, ethanol, butanol, and the like.

Step 4

The compound (Va) is hydrolyzed with acid or base in an alcoholic solvent, and the hydrolysate is refluxed in an organic solvent, if necessary under heating.

The former reaction is performed at a temperature in the range of from 0° to 100° C., preferably from 40° to 60° C., for 10 minutes to 3 hours, preferably 30 minutes to 1 hour.

The latter reaction is performed for 1 to 10 hours, preferably 3 to 5 hours under heating.

As an alcohol, the same alcohol as used in Step 3 may be used.

As the acid, hydrochloric acid, acetic acid, and the like may be used.

As the base, sodium hydroxide, potassium hydroxide, calcium hydroxide, potassium carbonate, pyridine, triethylamine, and the like may be used.

An organic solvent as mentioned in the above step 1 may be used.

Step 5

The compound (Ib) is reacted with the base in an alcohol to give the compound (Ia).

The reaction is performed at a temperature in the range of from 30° to 100° C., preferably about 50° C., for 5 minutes to 5 hours, preferably 5 minutes to 1 hour.

As an alcohol, the same alcohol used in Step 3 may be used.

As the base, alkali metal hydroxide such as sodium hydroxide and potassium hydroxide, and alkaline metal hydroxide such as calcium hydroxide may be used.

METHOD B

Step 1,2

Each reaction can be performed in the same manner as each step of Method A.

Step 3

The reaction mixture of the compound (IVa) and the mixture of an alcohol and an organic solvent is cooled to about from −80° to 0° C., and the solution is reacted with diethylmethoxyborane and $NaBH_4$. The reaction mixture is purified by column chromatography on silica gel to give the compound (Vb).

An alcohol and an organic solvent as mentioned above may be used.

The reaction is performed at a temperature in the range of from −120° to 0° C., preferably about −80° C., for 5 minutes to 5 hours, preferably 10 minutes to 3 hours.

Step 4

The compound (Vb) is hydrolyzed to give the compound (Ia).

The reaction may be conducted in a conventional manner for hydrolysis in the presence of usual catalysts including a basic compound such as sodium hydroxide and potassium hydroxide, and inorganic acid such as sulfate and hydrochloric acid.

Step 4'

The compound (Vb) is reacted with DDQ (2,3-dichloro-5,6-dicyano-1,4-benzoquinone) in an appropriate organic solvent to prepare the compound (VI).

The reaction is performed at a temperature in the range of from 0° to 100° C., preferably at room temperature, for 5 to 48 hours, preferably 8 to 20 hours.

An organic solvent which may be used are alcohols which are mentioned above, ethers, acetonitrile, and dioxane, most preferably dioxane.

Step 5

The compound (VI) is hydrolyzed in the same manner as Step 4 in Method B to prepare the compound (Ic).

METHOD C

The optically active compound (Ia) can be prepared by reacting the compound (III) with magnesium enolate A of optically active acetate in the manner disclosed in the literature (J. E. Lynch, Tetrahedron lett., 28, 1385 (1987)) (reference Example 15).

METHOD D

Step 1

The intermediate (VIII) prepared in Method C is reacted with t-butyldimethylsilyltrifluoromethanesulfonate to protect the hydroxy group with a t-butyldimethylsilyl group to obtain the compound (IX) [E. J. Corey, et al, Tetrahedron lett. 22, 3455–3458 (1981)].

The reaction is performed in an appropriate solvent at a temperature in the range of from 0° to 100° C., preferably at room temperature, for 10 minutes to 5 hours, preferably for 1 to 3 hours.

An organic solvent mentioned above can be used, most preferably methylene chloride.

Step 2

The compound (IX) is subjected to reduction with DIBAH (diisobutylaluminum hydride) to prepare the aldehyde compound (X).

The reaction is performed in an appropriate organic solvent at a temperature of the range of from −120° to 0° C., preferably from −70° to −60° C., for 10 minutes to 5 hours, preferably for 30 minutes to 1 hour.

As an organic solvent which may be used are ethers mentioned above, chloroform, hexane, THF, and the like, most preferably hexane.

Step 3

The compound (X) is reacted with bromodifluoroacetate in the presence of Zn to prepare the compound (XI) (Reformatski reaction).

The reaction is performed in an organic solvent such as ethers and THF at a temperature of the range of from 30° to 120° C., preferably about 70° C., for 10 minutes to 3 hours, preferably 15 minutes to 1 hour.

Step 4

The compound (XI) is reacted with tetrabutylammoniumfluoride to detach the silyl group to prepare the compound (Vb).

As an organic solvent which may be used are alcohols and ethers mentioned above, or basic and acidic solvent.

Step 5

The compound (Ia) can be prepared to hydrolyze the compound (Vb) in a conventional manner for hydrolysis (reference step 4 of Method B).

METHOD E

Step 1

The compound (III') can be prepared by the reaction of (1,3-dioxolan-2-ylmethyl)triphenylphosphonium bromide with the compound (II') in an organic solvent, preferably under heating.

The reaction is performed at a temperature in the range of from 0° to 200° C., preferably from room temperature to 120° C., for about 10 minutes to about 20 hours, preferably about 30 minutes to about 8 hours. An organic solvent which may be used are alcohols such as methanol and ethanol, ethers such as diethyl ether and tetrahydrofuran, dimethylformamide, acetonitrile and the like, most preferably dimethylformamide.

Step 2

The compound (III') is dissolved in an organic solvent and is added dropwise to a dianionic methyl acetoacetate solution (normally, obtained by reaction with sodium hydride and then butyllithium in THF) to give the compound (IVa').

The reaction is performed at a temperature under cooling in the range of from −80° to 0° C., for about 5 minutes to about 3 hours, preferably about 15 minutes to about 1 hour. An organic solvent as mentioned in the above step 1 may be used, most preferably tetrahydrofuran.

Step 3

A solution of the compound (IVa') in absolute ethanol/an organic solvent is cooled to −80°–0° C. and reacted with diethylmethoxyborane and $NaBH_4$, and the reaction mixture is subjected to column chromatography of silica gel to give the compound (Vb').

The reaction is performed at a temperature in the range of from −120°–0° C., preferably at about −80° C., for about 5 minutes to about 5 hours, preferably about 10 minutes to 3 hours. An organic solvent as mentioned above may be used.

Step 4

The compound (Vb') is hydrolyzed to prepare the compound (Ia').

The hydrolysis is performed in the same manner as Step 4 in Method B.

The compound of the present invention can be administered orally or parenterally. For example, the compound of the present invention may be orally administered in the form of tablets, powders, capsules, and granules, or liquid form such as syrup or elixir, and parenterally in the form of injection of aqueous or oily suspension.

These preparations can be prepared in a conventional manner by using excipients, binders, lubricants, aqueous or oily solubilizers, emulsifier, suspending agents, and the like. And further, preservatives and stabilizers can be used.

The dosage may be varied depending upon the administration route and age, weight, condition, and the kind of disease of the patients, usually 5–1000 mg/day, preferably 20–200 mg/day through oral route, and 1–500 mg/day, preferably 5–50 mg/day through parenteral route in a single or divided doses.

The present invention is illustrated by the following examples and reference examples, which are not to be considered as limiting.

The abbreviations used in examples and reference examples have the following meanings.

Me: methyl
Ph: phenyl
DMF: dimethylformamide
THF: tetrahydrofuran
iPr: isopropyl
BOC: t-butyloxycarbonyl
d.: diluted

EXAMPLE 1 (METHOD A)

Sodium (3R*,5S*)-(E)-7-[3-(4-fluorophenyl)-5-fluorobenzofuran-2-yl]-3,5-dihydroxy-6-heptenate (Ia-1)

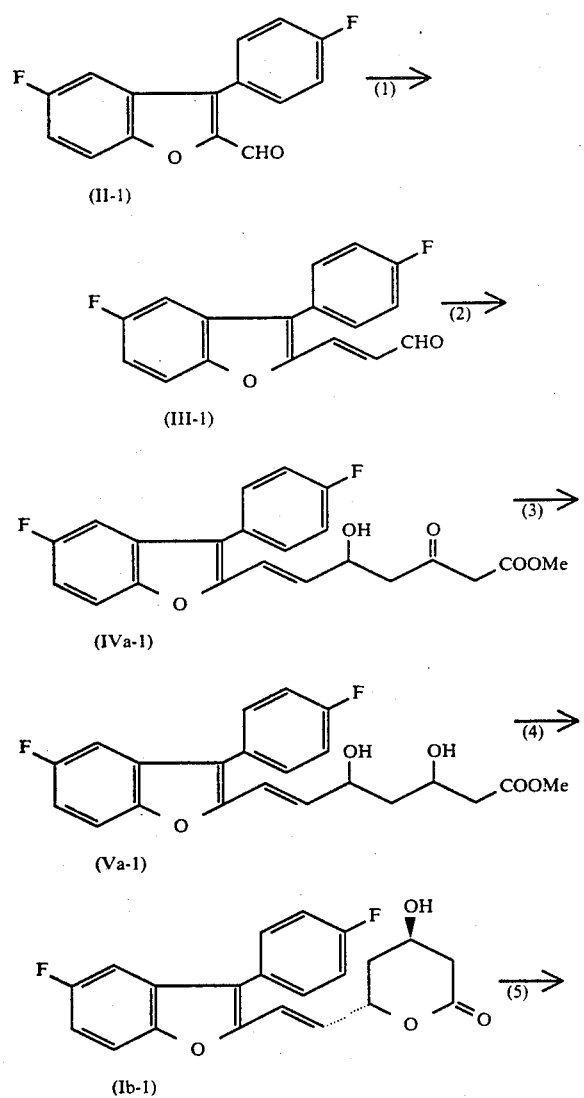

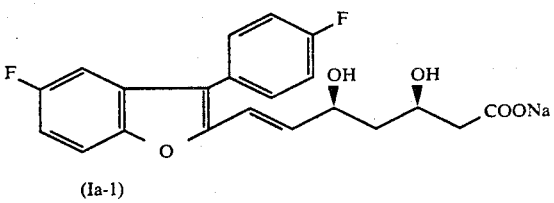

(1) To a mixture of 1 g of the compound (II), 4.62 g of [2-(1,3-dioxan-2-yl)methyl]triphenylphosphonium-bromide, and 20 ml of dry DMF is added dropwise a solution of 7.5 ml of n-butyllithium (1.59M hexane solution) in 20 ml of anhydrous methanol for 1 hour. The reaction mixture is poured into ice-water, the solution is extracted with acetic acid. The organic layer is washed with water, dried, and concentrated. To the residue are added 7 ml of c.HCl, 14 ml of water, and 20 ml of THF, and the mixture is stirred at room temperature for 15 minutes and concentrated. The residue is extracted with methylene chloride, and the organic layer is washed with water, dried and concentrated. The residue is subjected to column chromatography of silica gel eluting with methylene chloride to prepare 719 mg (Yield: 65%) of the objective compound (III-1). mp. 157°–159° C.

IR$\nu$ (Nujol) cm$^1$: 1671, 1610, 1118.

(2) A solution of 870 mg of methyl acetoacetate in dry THF is added dropwise to a solution of 3 mg of 60% NaH in dry THF. After evolution of hydrogen gas, to the mixture is added n-butyllithium (1.59M hexane solution). The reaction mixture is cooled to −70° C. and added dropwise a solution of 710 mg of the compound (III-1) in dry THF. The solution is stirred at the same temperature for 30 minutes and brought to 0° C. To the mixture is added dropwise 14 ml of 3N.HCl under cooling. The reaction mixture is extracted with ether, and the organic layer is washed with water, dried and concentrated. The residue is subjected to column chromatography of silica gel eluting with ethylacetate-n-hexane (1/1 v/v) to prepare 800 mg (Yield: 80%) of the objective compound (IVa-1).

IR$\nu$ (film) cm$^1$: 3475, 1710, 1220.

$^1$HNMR (CDCl$_3$)$\delta$: 2.78–2.95 (m, 2H); 3.52 (s, 2H); 3.75 (s, 3H); 3.72–3.74 (m, 1H); 4.80–4.90 (m, 1H); 6.50–7.50 (m, 9H)

(3) To a solution of 750 mg of the compound (IVa-1) in 7.5 ml of ether is added 142 mg of NaBH$_4$, under cooling, and the reaction mixture is reacted for 5 minutes and poured into acetic acid. The reaction mixture is extracted with ether, and the organic layer is washed with water, dried and concentrated. The residue is subjected to column chromatography of silica gel eluting with ethylacetate to prepare 643 mg (Yield: 85%) of the objective compound (Va-1).

IR$\nu$ (film) cm$^1$: 3400, 1720.

(4) A mixture of 643 mg of the compound (Va-1), 10 ml of methanol, 107 mg of NaOH, and 2.2 ml of water is stirred at room temperature for 10 minutes. After cooling, the mixture is mixed with 245 mg of acetic acid and extracted with ether. The organic layer is washed with water, dried and concentrated to distill ether. To the residue is added 20 ml of toluene, and the mixture is refluxed for 5 hours and concentrated. The residue is subjected to column chromatography of silica gel eluting with acetone/methylene chloride (1/5 v/v) to prepare 185 mg (Yield: 40%) of the objective compound (Ib-1).

IRν (film) cm¹: 3450, 1720.

¹HNMR (CDCl₃)δ: 1.70–2.20 (m, 3H); 2.60–2.70 (m, 2H); 4.40–4.50 (m, 1H); 5.32–5.45 (m, 1H); 6.48–6.75 (m, 2H); 6.95–7.50 (m, 7H).

(5) A mixture of 167 mg of the compound (Ib-1), 4.3 ml of methanol, and 4.28 ml of 0.1N.NaOH is heated at 50° C. for 5 minutes and concentrated to distill the solvent. The residue is extracted with ether, and the obtained aqueous layer is subjected to freeze-drying to prepare 128 mg (Yield: 69%) of the objective compound (Ia-1).

¹HNMR (CD₃OD)δ: 1.65–1.90 (m, 2H); 2.25–2.45 (m, 2H); 4.05–4.20 (m, 1H); 4.45–4.58 (m, 1H); 6.55–6.75 (m, 2H); 7.00–7.35 (m, 4H); 7.45–7.60 (m, 3H).

EXAMPLE 2 (METHOD A)

Sodium (3R*,5S*)-(E)-7-[3-(4-fluorophenyl)-7-isopropylbenzofuran-2-yl]-3,5-dihydroxy-6-heptenate (Ia-2)

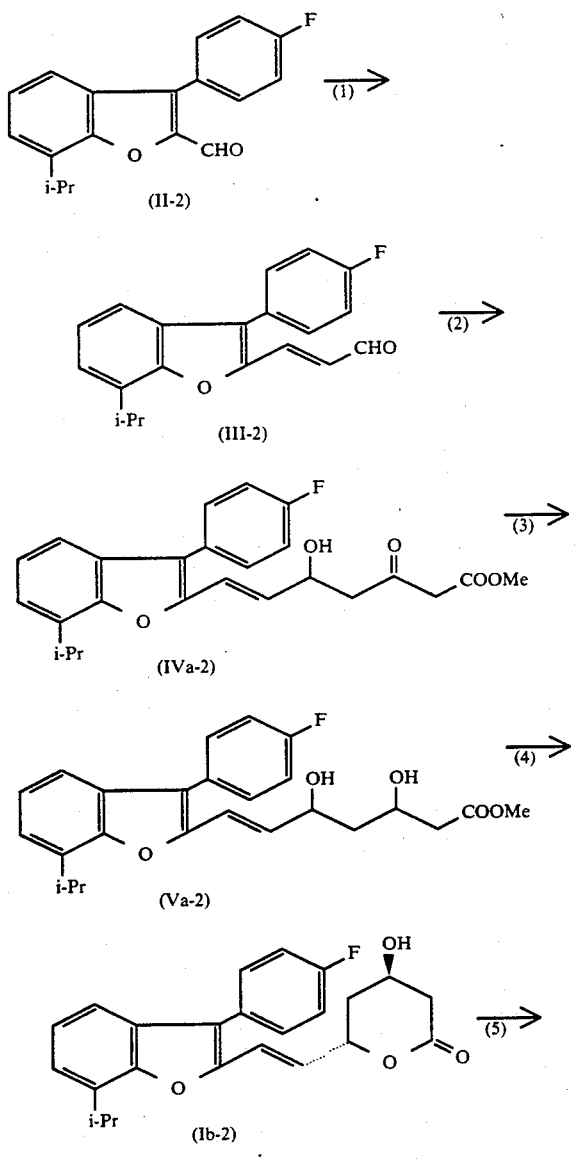

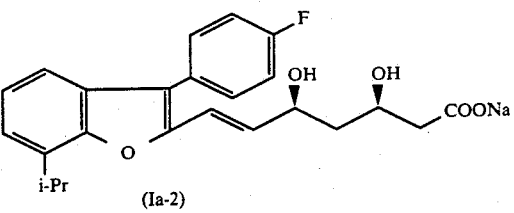

(1) To a mixture of 0.85 g of the compound (II-2), 3.59 g of [2-(1,3-dioxan-2-yl)methyl]triphenylphosphoniumbromide, 17 ml of dry DMF is added dropwise a solution of 5.68 ml of n-butyllithium (1.59M hexane solution) in 12 ml of absolute methanol under heating at 85° C. for 1 hour. The mixture is poured into ice-water, and the solution is extracted with ether. The ether layer is washed with water, dried and concentrated. The residue is mixed with 10 ml of HCl, 14 ml of water, and 10 ml of THF and stirred at room temperature for 30 minutes and concentrated. The residue is extracted with methylene chloride, and the organic layer is washed with aq.NaHCO₃, dried and concentrated. The residue is subjected to column chromatography of silica gel eluting with ethylacetate/hexane (1/10 v/v) to prepare 671 mg (Yield: 72.2%) of the objective compound (III-2).

¹HNMRδ: 1.42, 1.46 (each d, 6H, J=7.0 Hz); 3.49 (sept, 1H, J=6.5 Hz); 6.7 (dd, 1H, J=7.5 Hz, 12.5 Hz); 7.21–7.59 (m, 7H).

(2) To a solution of 330 mg of 60% NaH in dry THF is added dropwise 245 mg of methyl acetate in dry THF under nitrogen gas, and the mixture is stirred at 0° C. for 10 minutes. After evolution of hydrogen gas, to the mixture is added 1.33 ml of n-butyllithium (1.59M hexane). The reaction mixture is cooled to −78° C. and 650 mg of the compound (III-2) in dry THF is added dropwise thereto. The reaction mixture is stirred at the same temperature for 1 hour and poured into acetic acid under ice-cooling, and the solution is extracted with ether. The ether layer is washed with aq.NaHCO₃, dried, and concentrated. The residue is subjected to column chromatography of silica gel eluting with ethylacetate/n-hexane (1/5 v/v) to prepare 229 mg (Yield: 25.6%) of the objective compound (IVa-2).

¹HNMR (CDCl₃)δ: 1.41, 1.45 (each d, 6H, J=7.0 Hz); 2.85–2.95 (m, 2H); 3.40–3.60 (m, 3H); 3.75 (s, 3H); 4.85 (m, 1H); 6.53 (dd, 1H, J=9,15 Hz); 6.7 (dd, 1H, J=1,16 Hz); 7.15–7.55 (m, 7H).

(3) To a solution of 228 mg of the compound (IVa-2) in 4.0 ml of methanol is added 30 mg of NaBH₄, under cooling, and the mixture is reacted at 0° C. for 15 minutes and poured into acetic acid under cooling. The solution is neutralized with aq.NaHCO₃ and extracted with methylene chloride. The organic layer is washed with water, dried and concentrated. The residue is subjected to column chromatography of silica gel eluting with ethylacetate/hexane (1/1 v/v) to prepare 128 mg (Yield: 56%) of the objective compound (Va-2).

¹HNMR (CDCl₃)δ: 1.41, 1.45 (each d, 6H, J=7.0 Hz); 1.78 (m, 2H); 2.55 (m, 2H); 3.40 (sept, 1H, J=6.5 Hz); 3.71 (s, 3H); 4.35 (m, 1H) 4.17 (m, 1H).

(4) A mixture of 128 mg of the compound (Va-2), 6 ml of methanol, and 6 ml of NaOH is stirred at 50° C. for 30 minutes. After cooling, the reaction mixture is acidified with HCl and extracted with methylene chloride. The organic layer is washed with water, dried and concentrated. To the residue is added 10 ml of toluene, and the mixture is refluxed for 4.5 hours and concentrated. The residue is subjected column chromatography of silica gel eluting with acetone/methylene chloride (1/10 v/v) to prepare 23 mg (Yield: 44%) of the objective compound (Ib-2).

IR ν cm$^{-1}$: 290, 291.

$^1$HNMR (CDCl$_3$)δ: 1.41, 1.45 (each, d, 6H, J=7.0 Hz); 1.90-2.20 (m, 2H); 2.60-2.85 (m, 2H); 3.45 (sept, 1H); 4.61 (brs, 1H); 5.40 (m, 1H); 6.55 (dd, 1H, J=7, 15 Hz); 6.64 (dd, 1H, J=1,16 Hz); 7.10-7.50 (m, 7H).

(5) A mixture of 23 mg of the compound (Ib-2), 0.5 ml of methanol, and 0.5 ml of 0.1N.NaOH is heated at 50° C. for 1 hour and concentrated. The residue is extracted with ether, and the obtained aqueous layer is subjected to freeze-drying to prepare 17.1 mg (Yield: 74%) of the objective compound (Ia-2).

Anal Calcd. for (%) C$_{24}$H$_{24}$FO$_5$Na.H$_2$O: C, 63.70; H, 5.81; F, 4.18; Na 5.08. Found: C, 63.67; H, 5.97; F, 3.95; Na 5.34.

EXAMPLE 3 (METHOD A)

Sodium (3R*,5S*)-(E)-7-[5-chloro-3-(4-fluorophenyl)-7-isopropyl-4-methylbenzofuran-2-yl]-3,5-dihydroxy-6-heptenate (Ia-3)

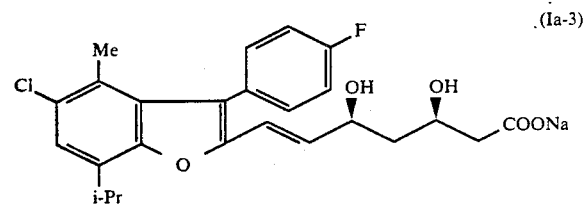

(Ia-3)

As a starting material, 1.2 g of the compound (II-3) is reacted in the same manner as Example 2 to prepare 23.3 mg of the objective compound (Ia-3) throuth 3-[5-chloro-3-(4-fluorophenyl)-7-isopropyl-4-methylbenzofuran-2-yl]-2-propenal (III-3), methyl 7-[5-chloro-3-(4-fluorophenyl)-7-isopropyl-4-methylbenzofuran-2-yl]-3-oxo-5-hydroxy-6-heptenate (IVa-3), methyl 7-[5-chloro-3-(4-fluorophenyl)-7-isopropyl-4-methylbenzofuran-2-yl]-3,5-dihydroxy-6-heptenate (Va-3), and 6-[5-chloro-3-(4-fluorophenyl)-7-isopropyl-4-methylbenzofuran-2-yl]ethenyl-4R*-hydroxy-3,4,5,6-tetrahydro-2H-pyran-2-one (Ib-3).

(III-3):
NMR (CDCl$_3$)δ: 1.37 (d, 6H, J=7.0 Hz); 2.08 (s, 3H); 3.40 (sept, 1H); 6.80 (dd, 1H, J=7.5, 16 Hz); 7.00-7.35 (m, 6H); 9.57 (d, 1H, J=2, 7 Hz).

(IVa-3):
NMR (CDCl$_3$)δ: 1.39 (d, 6H, J=7.0 Hz); 2.07 (s, 3H); 2.82-2.87 (m, 2H); 3.41 (sept, 1H); 3.48 (s, 2H); 3.72 (s, 3H); 4.74 (broad, 1H); 6.35-6.40 (m, 2H); 7.07-7.32 (m, 5H).

(Va-3):
NMR (CDCl$_3$)δ: 1.38 (d, 6H, J=7.0 Hz); 2.06 (s, 3H); 2.50-2.54 (m, 2H); 3.35-3.50 (m, 2H); 3.72 (s, 3H); 4.32 (broad, 1H); 4.58 (broad, 1H); 6.30-6.60 (m, 2H); 7.10-7.40 (m, 5H).

(Ib-3):
NMR (CDCl$_3$)δ: 1.33 (d, 6H, J=7.0 Hz); 1.83-2.15 (m, 2H); 2.03 (s, 2H); 2.58-2.82 (m, 2H); 3.38 (sept, 1H); 4.21 (broad, 1H); 5.22-5.35 (m, 1H).

(Ia-3):
Anal Calcd. (%) for C$_{25}$H$_{25}$ClFO$_5$Na.H$_2$O: C,59.94; H,5.42; Cl,7.07; F,3.99 Na,4.59. Found: C,59.65; H,5.49; Cl,6.95; F,4.01 Na,4.75.

EXAMPLE 4 (METHOD B)

Sodium (3R*,5S*)-(E)-7-[3-(4-fluoro-3-methylphenyl)-5-isopropyl-7-methylbenzofuran-4-yl]-3,5-dihydroxy-6-heptenate (Ia-4)

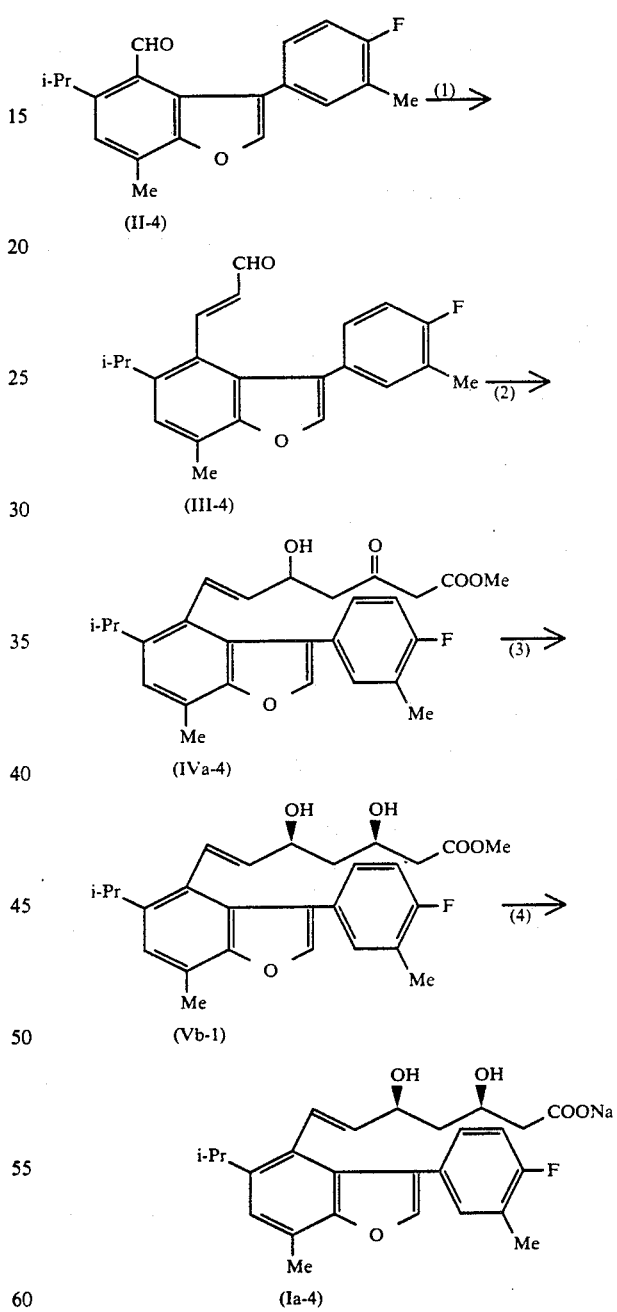

(1) To a mixture of 80 mg of the compound (II-4), 4 ml of dry DMF, and 307 mg of [2-(1,3-dioxan-2-yl)methyl]triphenylphosphonium bromide is added dropwise a solution of 0.49 ml of n-butyllithium (1.59M hexane) in 2 ml of absolute methanol at about 80° C., and the mixture is stirred at the same temperature through 15 minutes and concentrated. The residue is mixed with 6N.HCl and stirred at room temperature for 15 minutes. The reaction mixture is neutralized with NaHCO$_3$ and extracted with methylene chloride. The organic layer is washed with water, dried and concentrated. The residue is subjected to column chromatography of silica gel eluting with n-hexane to prepare 40 mg of the objective compound (III-4).

IR (Nujol) cm$^{-1}$: 1670, 1600, 1130.

(2) The compound (III-4) 40 mg is reacted in the same manner as Example 2 (2) to prepare 31 mg of the objective compound (IVa-4).

IR (film) cm$^{-1}$: 3400, 1720.

(3) A mixture of 31 mg of the compound (IVa-4), 2 ml of dry THF, and 1 ml of methanol is cooled to $-70°$ C., and 0.1 ml of a solution of diethylmethoxyboran in THF is added dropwise thereto. The mixture is reacted for 15 minutes, mixed with 4 mg of NaBH$_4$, and stirred for 1 hour. The reaction mixture is poured into acetic acid, and the solution is basified with NaHCO$_3$ and extracted with ether. The ether layer is washed with water, dried and concentrated. The residue is subjected to column chromatography of silica gel eluting with ethyl acetate/n-hexane (½ v/v) to prepare 21 mg of the compound (Vb-1).

IR$\nu$ (film) cm$^{-1}$: 3350, 1720, 1230, 1190.

(4) The compound (Vb-1) 21 mg is dissolved in a mixture of 0.5 ml of methanol and 0.44 ml of NaOH. The solution is heated at 50° C. on water bath for 15 minutes and concentrated. The residue is extracted with ether, the resulting aqueous layer is subjected to freeze-dry to prepare 10 mg of the objective compound (Ia-4).

Anal Calcd. (%) for C$_{26}$H$_{28}$FO$_5$Na.2H$_2$O C, 62.64; H, 6.47. Found: C, 62.26; H, 6.31.

$^1$HNMR (CD$_3$OD)$\delta$: 1.25, 1.26 (each d, 6H, J=7.0 Hz); 1.78–2.00 (m, 2H); 2.30–2.43 (m, 5H); 2.53 (s, 3H); 3.30–3.45 (m, 1H); 4.10–4.25 (m, 1H); 4.52–4.63 (m, 1H); 6.11 (dd, 1H, J=7,15 Hz); 6.96–7.17 (m, 3H); 7.32 (s, 1H); 7.70–7.81 (m, 2H).

EXAMPLE 5

Sodium (3R*,5S*)-(E)-7-[3-isopropyl-7-(4-fluorophenylbenzofuran-2-yl]-3,5-dihydroxy-6-heptenate (Ia-5)

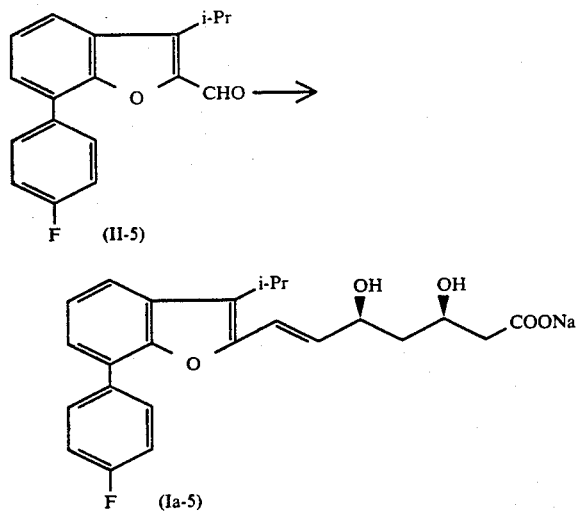

As a starting material, 616 mg of 2-formyl-7-(4-fluorophenyl)-3-isopropylbenzofuran (II-5) is reacted in the same manner as Example 4 (1)–(4) to prepare 41 mg of the objective compound (Ia-5) through 3-[7-(4-fluorophenyl)-3-isopropylbenzofuran-2-yl]-2-propenal (III-5), methyl 7-[7-(4-fluorophenyl)-3-isopropylbenzofuran-2-yl]-3-oxo-5-hydroxy-6-heptenate (IVa-5), and (3R*,5S*) methyl 7-[7-(4-fluorophenyl)-3-isopropylbenzofuran-2-yl]-3,5-dihydroxy-6-heptenate (Vb-2) as intermediate products.

(III-5):
NMR (CDCl$_3$): 1.51 (d, 6H, J=7.0 Hz); 3.37 (sept, 1H); 6.77 (dd, 1H, J=7.5,16 Hz); 7.15–7.35 (m, 3H); 7.46–7.54 (m, 2H); 7.67–7.83 (m, 3H); 9.72 (d, 1H, J=15 Hz).

(IVa-5):
NMR (CDCl$_3$): 1.43 (d, 6H, J=7.0 Hz); 2.90–2.97 (m, 2H); 3.25 (sept, 1H); 3.52 (s, 2H); 3.75 (s, 1H); 4.80–4.92 (m, 1H); 6.31 (dd, 1H, J=7.5, 16 Hz); 6.76 (dd, 1H, J=1,16 Hz); 7.14–7.35 (m, 4H); 7.60–7.65 (m, 1H); 7.78–7.85 (m, 2H).

(Vb-2):
NMR (CDCl$_3$): 1.42 (d, 6H, J=7.0 Hz); 1.73–1.83 (m, 2H); 2.53 (d, 2H, J=7.0 Hz); 3.25 (sept, 1H); 3.73 (s, 3H); 6.33 (dd, 1H, J=6, 15 Hz); 7.15–7.35(m, 4H); 7.58–7.65 (m, 1H); 7.79–7.89 (m, 2H).

(Ia-5):
NMR (CD$_3$OD): 1.43 (d, 6H, J=7.0 Hz); 1.75–1.90 (m, 2H); 2.30–2.50 (m, 2H); 4.05–4.20 (m, 1H); 4.43–4.60 (m, 1H); 6.38 (dd, 1H, J=7, 16 Hz); 7.20–7.40 (m, 4H); 7.58–7.63 (m, 1H); 7.80–7.93 (m, 2H).

Anal Calcd. (%) for C$_{24}$H$_{24}$FNaO$_5$.2H$_2$O: C,61.27; H,5.73; F,4.03; Na,4.90. Found: C,61.36; H,5.61; F,4.06; Na,5.04.

EXAMPLE 6

Sodium (3R*,5S*)-(E)-7-[2-(4-fluoro-3-methylphenyl)-4-isopropyl-7-methylbenzofuran-3-yl]-3,5-dihydroxy-6-heptenate (Ia-6)

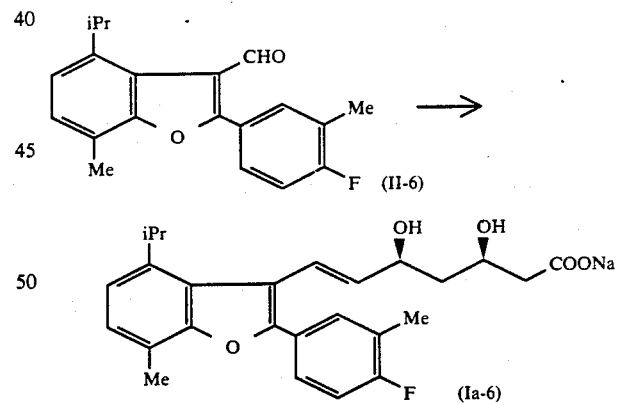

As a starting material, 3-formyl-2-(4-fluoro-3-methylphenyl)-4-isopropyl-7-methylbenzofuran (II-6) is reacted in the same manner as Example 4 (1)–(4) to prepare 43 mg of the objective compound (Ia-6) through 3-[2-(4-fluoro-3-methylphenyl)-4-isopropyl-7-methylbenzofuran-3-yl]-2-propenal (III-6), methyl 7-[2-(4-fluoro-3-methylphenyl)-4-isopropyl-7-methylbenzofuran-3-yl]-3-oxo-5-hydroxy-6-heptenate (IVa-6), and (3R*,5S*) methyl 7-[2-(4-fluoro-3-methylphenyl)-4-isopropyl-7-methylbenzofuran-3-yl]-3-oxo-5-hydroxy-6-heptenate (Vb-3).

(III-6):

¹HNMR (CDCl₃): 1.35 (d, 6H, J=7.0 Hz); 2.33 (d, 3H, J=1 Hz); 2.52 (s, 3H); 3.49 (sept, 1H); 6.42 (dd, 1H, J=7.5, 16 Hz); 7.08-7.13 (m, 3H); 7.48-7.60 (m, 2H); 7.90 (d, 1H); 9.70 (d, 1H, J=15 Hz).

(IVa-6):
¹HNMR (CDCl₃): 1.29 (d, 6H, J=7.0 Hz); 2.34 (d, 3H, J=1 Hz); 2.51 (s, 3H); 2.78 (d, 2H, J=6 Hz); 3.50-3.62 (m, 2H); 3.75 (s, 3H); 4.74-4.83 (m, 1H); 5.79 (dd, 1H, J=6,15 Hz); 6.95 (dd, 1H, J=1,16 Hz); 7.04-7.09 (m, 3H); 7.55-7.70 (m, 2H).

(Vb-3):
¹HNMR (CDCl₃): 1.29 (d, J=7.0 Hz, 6H); 1.60-1.80 (m, 2H); 2.32 (d, 3H, J=1 Hz); 2.45-2.65 (m, 5H); 3.59 (sept, 1H); 3.74 (s, 3H); 4.26-4.40 (m, 1H); 4.46-4.63 (m, 1H); 5.81 (dd, 1H, J=6, 16 Hz); 6.91 (dd, 1H, J=1,16 Hz); 7.00-7.09 (m, 3H); 7.60-7.75 (m, 2H).

(Ia-6):
¹HNMR (CD₃OD): 1.27 (d, 6H, J=7.0 Hz); 1.60-1.83 (m, 2H); 2.31-2.40 (m, 4H); 2.47 (s, 3H); 3.68 (sept, 1H); 4.04-4.18 (m, 1H); 4.06-4.14 (m, 1H); 5.82 (dd, 1H, J=6, 16 Hz); 6.87 (dd, 1H, J=1, 17 Hz); 7.02-7.13 (m, 3H); 7.64-7.80 (m, 2H).

Anal Calcd. (%) for C₂₆H₂₈FNaO₅·1.5H₂O: C,66.23; H,6.15; F,4.02; Na,4.87. Found: C,66.00; H,6.23; F,3.90; Na,5.01.

EXAMPLE 7

Sodium (3R*,5S*)-(E)-7-[2-(4-fluorophenyl)-4-isopropyl-7-methylbenzofuran-3-yl]-3,5-dihydroxy-6-heptenate (Ia-7)

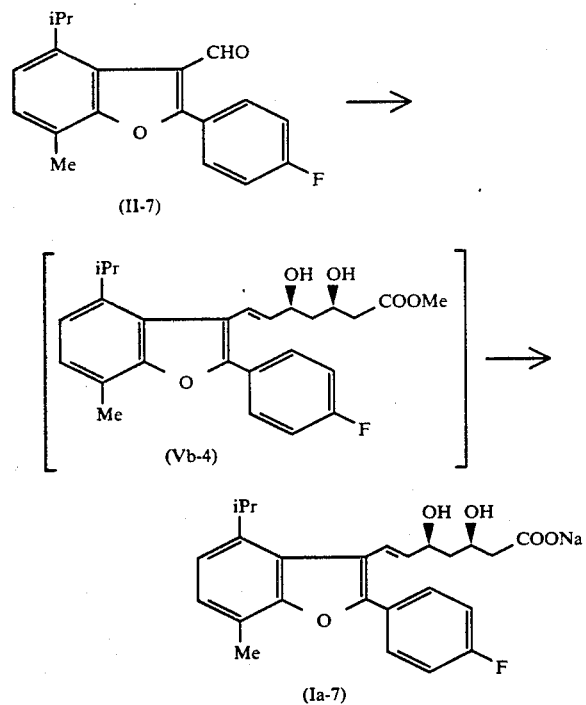

As a starting material, 450 mg of 3-formyl-2-(4-fluorophenyl)-4-isopropyl-7-methylbenzofuran (II-7) is reacted in the same manner as Example 4 (1)-(4) to prepare 32.9 mg of the objective compound (Ia-7) through 3-[2-(4-fluorophenyl)-4-isopropyl-7-methylbenzofuran-3-yl]-2-propenal (III-7), methyl 7-[2-(4-fluorophenyl)-4-isopropyl-7-methylbenzofuran-3-yl]-3-oxo-5-hydroxy-6-heptenate (IVa-7), and methyl 7-[2-(4-fluorophenyl)-4-isopropyl-7-methylbenzofuran-3-yl]-3,5-dihyroxy-6-heptenate (Vb-4).

(III-7): mp. 118°-120° C.
¹HNMR (CDCl₃)δ: 1.35 (d, 6H, J=6.8 Hz); 2.51 (s, 3H); 3.48 (sept, 1H, J=6.8 Hz); 6.42 (dd, 1H, J=7.7, 16 Hz); 7.10-7.22 (m, 3H); 7.68-7.69 (m, 2H); 7.90 (d, 1H, J=16.0 Hz); 9.71 (d, 1H, J=7.7 Hz).
IR (CHCl₃) cm⁻¹: 1674.

(IVa-7):
¹HNMR (CDCl₃)δ: 1.30 (d, 6H, J=6.8 Hz); 2.51 (s, 3H); 2.80 (d, 2H, J=6.2 Hz); 3.50 (s, 2H); 3.55 (sept, 1H, J=6.8 Hz); 3.75 (s, 3H); 4.73-4.83 (m, 1H); 5.80 (dd, 1H, J=5.6, 16.0 Hz); 6.96 (dd, 1H, J=1.5, 16.0 Hz); 7.04-7.24 (m, 4H); 7.79-7.86 (m, 2H).
IR (CDCl₃) cm⁻¹: 3592, 3558, 1741, 1709.

(Vb-4):
¹HNMR (CDCl₃)δ: 1.24 (d, 6H, J=7.0 Hz); 1.53-1.75 (m, 2H); 2.05-2.39 (m, 2H); 2.46 (s, 3H); 2.49 (d, 2H, J=3.2 Hz); 3.55 (sept, 1H, J=7.0 Hz); 3.68 (s, 3H); 4.18-4.22 (m, 1H); 4.44-4.59 (m, 1H); 5.77 (dd, 1H, J=5.8, 15.6 Hz); 6.86 (dd, 1H, J=1.2,5.8 Hz); 7.01-7.10 (m, 4H); 7.77-7.84 (m, 2H).

(Ia-7):
¹HNMR (CD₃OD): 1.26 (d, 6H, J=6.8 Hz); 1.54-1.87 (m, 2H); 2.27-2.39 (m, 2H); 2.46 (s, 3H); 3.67 (sept, 1H, J=6.8 Hz); 4.01-4.16 (m, 1H); 4.42-4.55 (m, 1H); 5.71 (dd, 1H, J=6.2, 15.8 Hz); 6.88 (dd, 1H, J=1.2, 15.8 Hz); 6.97-7.24 (m, 4H); 7.87-7.94 (m, 2H) SIMS m/z: 449 (M+H)⁺, 471 (M+Na)⁺, 919 (2M+Na)⁺.

EXAMPLE 8

Sodium 7-[2-(4-fluorophenyl)-4-isopropylbenzofuran-7-methyl-3-yl]-3-hydroxy-5-oxo-6-heptenate (Ic-1)

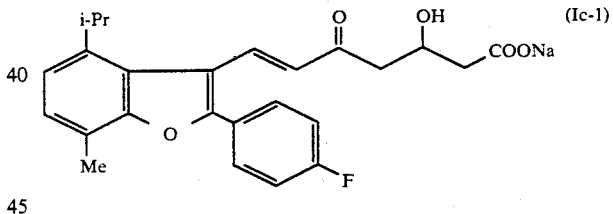

To the compound (Vb-4), which was obtained in Example 7 as an intermediate product, are added 3 ml of dioxane and 25 mg of DDQ, and the mixture is left at room temperature for 15 minutes and concentrated. The residue is subjected to column chromatography of silica gel eluting with ethyl acetate/n-hexane (1/1 v/v) to prepare 24.2 mg of methyl 7-[2-(4-fluorophenyl)-4-isopropylbenzofuran-7-methyl-3-yl]-3-hydroxy-5-oxo-6-heptenate (VI-1). To the solution of the compound (VI-1) in methanol is added 0.1N.NaOH, and the mixture is stirred at 50° C. for 2.5 hours and concentrated. The residue is extracted with ether, the obtained aqueous layer is subjected to freeze-dry to prepare 15.9 mg (Yield: 65%) of the compound (Ic-1).

(Ic-1):
¹HNMR (CD₃OD)δ: 1.32 (d, 6H, J=6.8 Hz); 2.35-2.44 (m, 2H); 2.50 (s, 3H); 2.76-2.90 (m, 2H); 3.54 (sept, 1H, J=6.8 Hz); 4.36-4.51(m, 1H); 6.49 (d, 1H, J=16.2 Hz); 7.06-7.36 (m, 4H); 7.81-7.88 (m, 2H); 8.05 (d, 1H, J=16.2 Hz).
SIMS m/z: 447 (M+H)⁺, 469 (M+Na)⁺, 915 (2M+Na)⁺.

EXAMPLE 9

Sodium (3R*,5S*)-(E)-7-[4-(4-fluorophenyl)-2-isopropylbenzofuran-3-yl]-3,5-dihydroxy-6-heptenate (Ia-8)

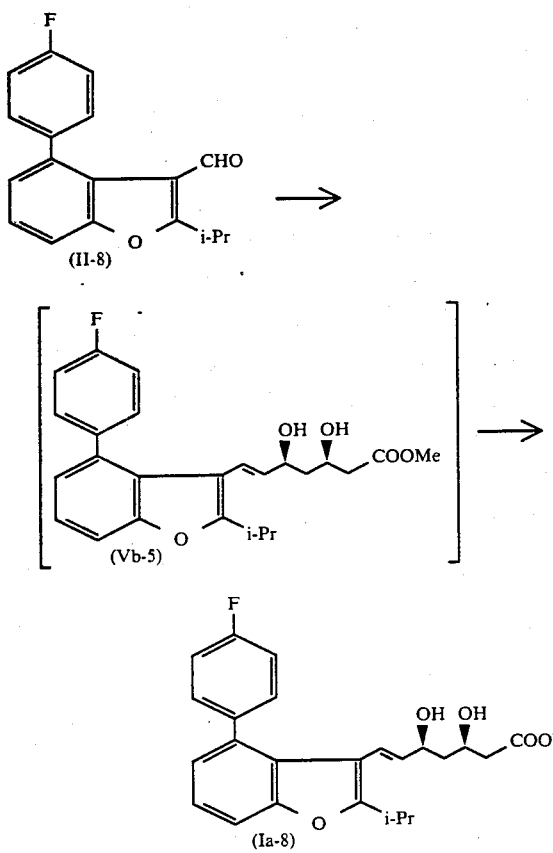

As a starting material, 450 mg of 3-formyl-4-(4-fluorophenyl)-2-isopropylbenzofuran (II-8) is subjected to react in the same manner as Example 4 (1)–(4) to prepare 28.1 mg of the objective compound (Ia-8) through 3-[4-(4-fluorophenyl)-2-isopropylbenzofuran-3-yl]-2-propenal (III-8), methyl 7-[4-(4-fluorophenyl)-2-isopropylbenzofuran-3-yl]-3-oxo-5-hydroxy-6-heptenate (IVa-8), and (3R*,5S*) methyl 7-[4-(4-fluorophenyl)-2-isopropylbenzofuran-3-yl]-3,5-dihydroxy-6-heptenate (Vb-5) as intermediate product.

(III-8):
$^1$HNMR (CDCl$_3$)δ: 1.39 (d, 6H, J=6.8 Hz); 3.35 (s, 1H, J=6.8 Hz); 5.95 (dd, 1H, J=7.8, 16.4 Hz); 7.00 (d, 1H, J=16.4 Hz); 7.08–7.17 (m, 3H); 7.29–7.39 (m, 3H); 7.45–7.51 (m, 1H); 9.21 (d, 1H, J=7.8 Hz).

(IVa-8):
$^1$HNMR (CDCl$_3$)δ: 1.34 (d, 6H, J=6.8 Hz); 2.49 (brs, 1H); 2.54–2.59 (m, 2H); 3.48 (s, 2H); 3.76 (s, 3H); 4.40–4.52 (m, 1H); 5.36 (dd, 1H, J=6.0, 16.0 Hz); 6.06 (dd, 1H, J=1.2, 6.0 Hz); 7.05–7.22 (m, 3H); 7.30–7.45 (m, 4H).

(Vb-5): mp. 92°–95° C.
$^1$HNMR (CDCl$_3$)δ: 1.35 (d, 6H, J=7.0 Hz); 1.41–1.69 (m, 2H); 2.47–2.53 (m, 2H); 2.93 (brs, 1H); 3.29 (sept, 1H, J=7.0 Hz); 3.64 (brs, 1H); 4.13–4.32 (m, 2H); 5.38 (dd, 1H, J=6.4, 15.8 Hz); 6.03 (dd, 1H, J=1.0, 15.8 Hz); 7.04–7.14 (m, 3H); 7.23–7.46 (m, 4H).

(Ia-8):
$^1$HNMR (CD$_3$OD): 1.34, 1.35 (each d, 6H, J=6.8 Hz); 1.41–1.74 (m, 2H); 2.15–2.52 (m, 2H); 3.39 (sept, 1H, J=6.8 Hz); 3.91–4.18 (m, 2H); 5.48 (dd, 1H, J=7,16 Hz); 5.59 (dd, 1H, J=0.8,16.0 Hz); 7.03–7.43 (m, 7H).
SIMS m/z: 457 (M+Na)$^+$, 891 (2M+Na)$^+$, 913 (2M+2NaH)$^+$.

EXAMPLE 10

Sodium 7-[4-(4-fluorophenyl)-2-isopropylbenzofuran-3-yl]-3-hydroxy-5-oxo-6-heptenate (Ic-2)

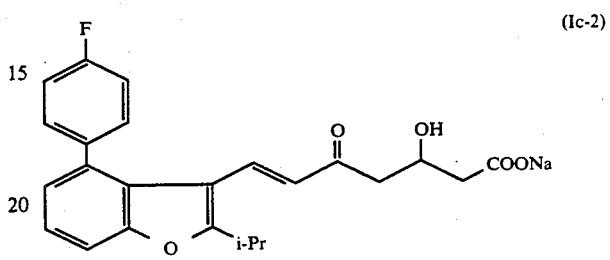

The compound (Vb-5), which was prepared in Example 9 as intermediate product, is reacted in the same manner as Example 8 to prepare 11.4 mg of the compound (Ic-2) through methyl 7-[4-(4-fluorophenyl)-2-isopropylbenzofuran-3-yl]-3-hydroxy-5-oxo-6-heptenate (VI-2).

(VI-2):
$^1$HNMR (CDCl$_3$)δ: 1.38 (d, 6H, J=6.9 Hz); 2.39 (d, 2H, J=6.0 Hz); 2.46–2.51 (m, 2H); 3.37 (sept, 1H, J=6.9 Hz); 4.37–4.50 (m, 1H); 5.72 (d, 1H, J=16.5 Hz) 7.10–7.51 (m, 8H).

(Ic-2):
$^1$HNMR (CD$_3$OD)δ: 1.39 (d, 6H, J=6.8 Hz); 2.25–2.32 (m, 2H); 2.43–2.50 (m, 2H); 3.44 (sept, 1H, J=6.8 Hz); 4.24–4.37 (m, 1H); 5.85 (d, 1H, J=16.2 Hz); 7.13–7.53 (m, 8H).
SIMS m/z: 433 (M+H)$^+$, 4.55 (M+Na)$^+$, 887 (2M+Na)$^+$.

EXAMPLE 11

Sodium (3R*,5S*)-(E)-7-[5-(4-fluoro-3-methylphenyl)-3-isopropylbenzofuran-4-yl]-3,5-dihydroxy-6-heptenate (Ia-9)

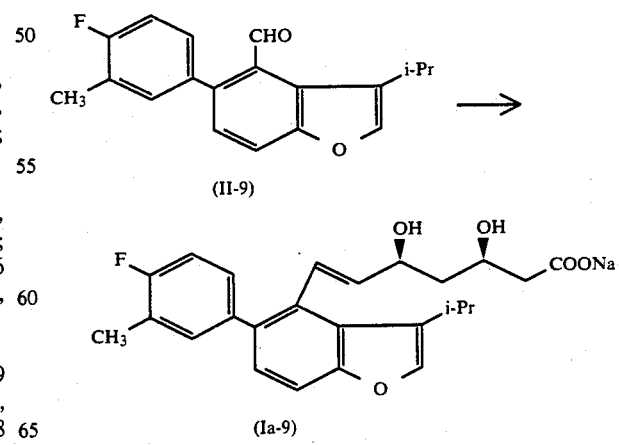

As a starting material, 50 mg of 4-formyl-5-(4-fluoro-3-methylphenyl)-3-isopropylbenzofurnan (II-9) is reacted in the same manner as Example 7 to prepare 10.5 mg of the objective compound (Ia-9) through 3-[5-(4-fluoro-3-methylphenyl)-3-isopropylbenzofuran-4-yl]-2-propenal (III-9), methyl 7-[5-(4-fluoro-3-methylphenyl)-3-isopropylbenzofuran-4-yl]-3-oxo-5-hydroxy-6-heptenate (IVa-9), and methyl 7-[5-(4-fluoro-3-methylphenyl)-3-isopropylbenzofuran-4-yl]-3,5-dihydroxy-6-heptenate (Vb-6).

(III-9):

$^1$HNMR (CDCl$_3$)δ: 1.29 (d, 6H, J=7 Hz); 2.30 (d, 3H, J=1.6 Hz); 3.15 (sept, 1H, J=7 Hz); 5.99 (dd, 1H, J=7.8, 16 Hz); 6.97–7.54 (m, 6H); 7.90 (d, 1H, J=16 Hz); 9.57 (d, 1H, J=7.8 Hz).

(IVa-9):

$^1$HNMR (CDCl$_3$)δ: 1.29 (dd, 6H, J=1.4, 6.8 Hz); 2.31 (d, 3H, J=1.8 Hz); 2.48 (brs, 1H); 2.50–2.55 (m, 2H); 3.22 (d, sept, 1H, J=1.4, 6.8 Hz); 3.44 (s, 2H); 3.75 (s, 3H); 4.55–4.67 (m, 1H); 5.35 (dd, 1H, J=6, 15.6 Hz); 6.90–7.44 (m, 7H).

(Vb-6):

$^1$HNMR (CDCl$_3$)δ: 1.25–1.32 (m, 6H); 1.36–1.59 (m, 2H); 2.29 (d, 3H, J=1.8 Hz); 2.43–2.48 (m, 2H); 3.14–3.37 (m, 1H); 3.73 (s, 3H); 4.06–4.22 (m, 1H); 4.36–4.47 (m, 1H); 5.38 (dd, 1H, J=6,16 Hz); 6.87–7.45 (m, 7H).

(Ia-9):

$^1$HNMR (CD$_3$OD)δ: 1.31 (d, 6H, J=7 Hz); 1.34–1.66 (m, 2H); 2.12–2.43 (m, 2H); 3.35 (sept, 1H, J=7 Hz); 3.77–3.92 (m, 1H); 4.23–4.36 (m, 1H); 5.39 (dd, 1H, J=6,16 Hz); 6.85,7.56 (m, 7H).

SIMS m/z: 449 (M+H)$^+$, 471 (M+Na)$^+$, 897 (2M+H)$^+$, 919 (2M+Na)$^+$, 941 (2M+2Na-H)$^+$.

EXAMPLE 12

Sodium (3R*,5S*)-(E)-7-[3-(4-fluoro-3-methylphenyl)-7-isopropylbenzofuran-2-yl]-3,5-dihydroxy-6-heptenate (Ia-10)

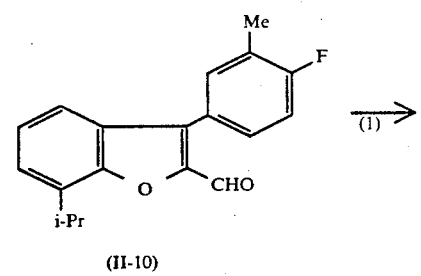

(II-10)

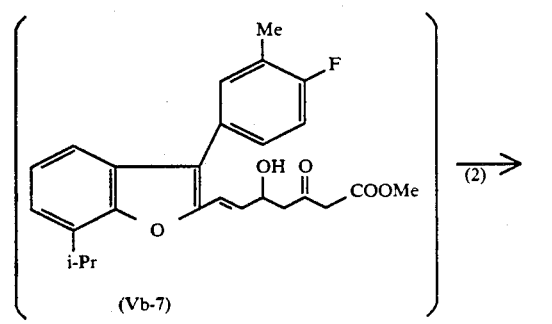

(Vb-7)

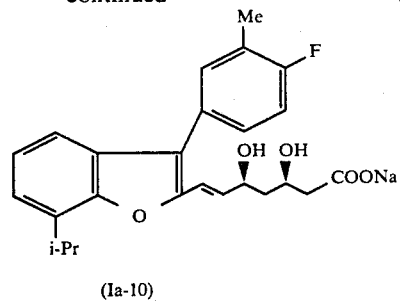

(Ia-10)

As a starting material, 1.7 g of 2-formyl-3-(4-fluoro-3-methylphenyl)-7-isopropylbenzofuran (II-10) is reacted in the same manner as Example 4 to prepare 33 mg of the objective compound (Ia-10) through 3-[3-(4-fluoro-3-methylphenyl)-7-isopropylbenzofuran-2-yl]-2-propenal (III-10), methyl 7-[3-(4-fluoro-3-methylphenyl)-7-isopropylbenzofuran-2-yl]-3-oxo-5-hydroxy-6-heptenate (IVa-10), and (3R*,5S*) methyl 7-[3-(4-fluoro-3-methylphenyl)-7-isopropylbenzofuran-2-yl]-3-oxo-5-hydroxy-6-heptenate (Vb-7) as intermediate product.

(III-10):

$^1$HNMR (CDCl$_3$): 1.44 (d, 6H, J=7 Hz); 2.39 (d, 3H, J=1.5 Hz); 3.49 (sept, 1H); 6.92 (dd, 1H); 7.15–7.47 (m, 7H); 9.61 (d, 1H, J=7.5 Hz).

(IVa-10):

$^1$HNMR (CDCl$_3$): 1.43 (d, J=7.0 Hz, 6H); 2.36 (d, 3H, J=1.5 Hz); 2.85–2.92 (m, 3H); 3.49 (sept, 1H); 3.52 (s, 3H); 3.74 (s, 3H); 4.70–4.90 (m, 1H); 6.51 (dd, 1H, J=6,16 Hz); 6.73 (dd, 1H, J=1,17 Hz); 7.10–7.40 (m, 6H).

(Vb-7):

$^1$HNMR (CDCl$_3$): 1.42 (d, 6H, J=7.0 Hz); 1.76–1.90 (m, 2H); 2.35 (d, 3H, J=1.5 Hz); 2.52–2.55 (m, 2H); 3.18–3.58 (m, 2H); 3.72 (s, 3H); 4.30–4.4 (m, 1H); 4.60–4.70 (m, 1H); 6.54 (dd, 1H, J=6,15 Hz); 6.70 (dd, 1H, J=1,15 Hz); 7.08–7.40 (m, 6H).

(Ia-10):

$^1$HNMR (CD$_3$OD): 1.42 (d, 6H, J=7.0 Hz); 1.70–1.90 (m, 2H); 2.34 (m, 8H); 3.47 (sept, 1H); 4.05–4.18 (m, 1H); 4.45–4.55 (m, 1H); 6.55 (dd, 1H, J=6,15 Hz); 6.70 (dd, 1H, J=1,15 Hz); 7.10–7.40 (m, 6H).

Anal Calcd. (%) for C$_{25}$H$_{26}$FNaO$_5$·½H$_2$O: C, 69.15; H, 5.51; F, 4.00; Na, 4.83. Found: C, 63.33; H, 5.88; F, 3.91; Na, 5.13.

EXAMPLE 13

Sodium 7-[3-(4-fluoro-3-methylphenyl)-7-isopropylbenzofuran-2-yl]-3-hydroxy-5-oxo-6-heptenate (Ic-3)

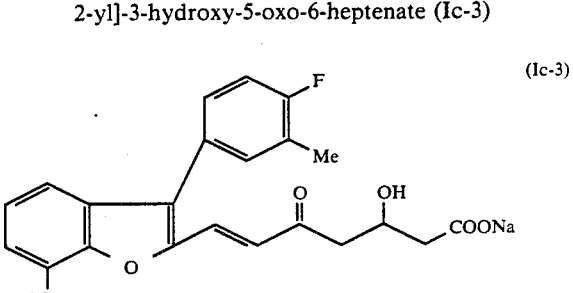

(Ic-3)

As a starting material, 50 mg of the compound (Vb-7), which was prepared in Example 12, is reacted in the same manner as Example 12 to prepare 26 mg (Yield: 58.7%) of the objective compound (Ic-3) through methyl 7-[3-(4-fluoro-3-methylphenyl)-7-isopropylbenzofuran-2-yl]-3-hydroxy-5-oxo-6-heptenate (VI-3) as an intermediate product.

(VI-3):

¹HNMR (CDCl₃): 1.41 (d, 6H, J=7.0 Hz); 2.35 (d, 3H, J=1 Hz); 2.58 (d, 2H, J=6 Hz); 2.90 (d, 2H, J=6 Hz); 3.40–3.60 (m, 2H); 3.72 (s, 3H); 4.58 (sept, 1H); 6.95 (d, 1H, J=20 Hz); 7.50–7.43 (m, 6H); 7.51 (d, 1H, J=15 Hz).

(Ic-3):

¹HNMR (CDCl₃): 1.41 (d, 6H, J=7.0 Hz); 2.29–3.39 (m, 6H); 2.80–2.88 (m, 1H); 3.40–3.55 (m, 1H); 4.38–4.50 (m, 1H); 6.98 (d, 1H, J=15 Hz); 7.20–7.48 (m, 6H); 7.51 (d, 1H, J=15 Hz).

EXAMPLE 14

Sodium (3R*,5S*)-(E)-7-[3-(4-fluoro-3-methylphenyl)-7-isopropylbenzofuran-2-yl]-3,5-dihydroxyheptenate (Ia-11)

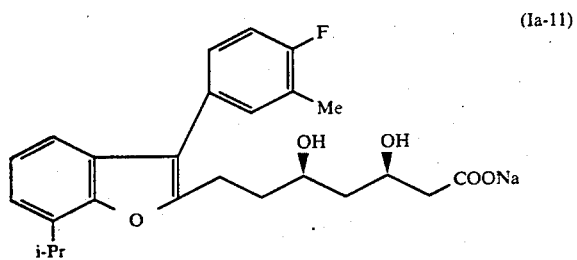

(Ia-11)

To a solution of 40 mg of the compound (Vb-1) obtained in Example 12 in 1 ml of methanol is subjected to catalytic reduction over 40 mg of 5% Pd-C. The reaction mixture is filtered, and the filtrate is concentrated and subjected to column chromatography of silica gel eluting with ethyl acetate/hexane (½), and the obtained product is treated in the same manner as Example 4(4) to prepare 8 mg of the objective compound (Ia-11).

NMR (CDCl₃): 1.25–1.50 (m, 10H); 1.75–1.83 (m, 1H); 2.18–2.30 (m, 4H); 2.82–2.90 (m, 1H); 3.78–3.85 (m, 1H); 6.78–7.40 (m, 6H).

EXAMPLE 15

Sodium (3R,5S)-(E)-7-[4-(4-fluorophenyl)-2-isopropylbenzofuran-3-yl]-3,5-dihydroxy-6-heptenate (Ia-12)

Synthesis of Optically Isomer of the Compound (Ia-8)

(III-8) 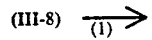

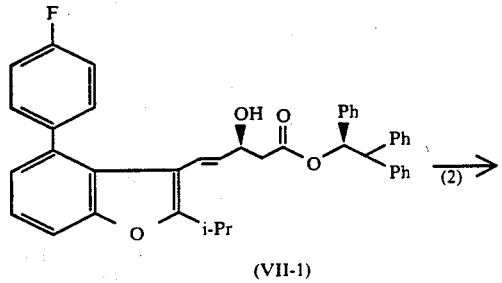

(VII-1)

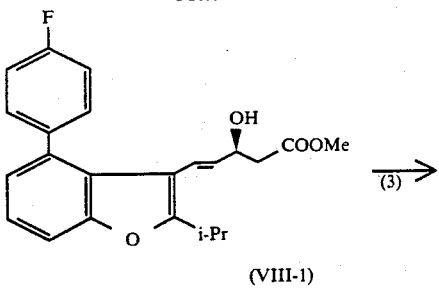

(VIII-1)

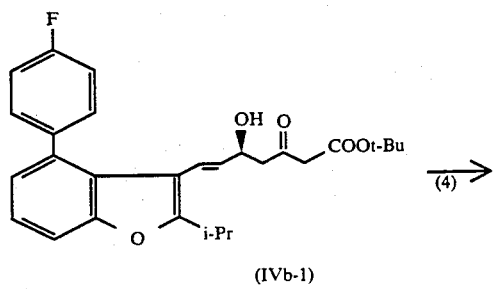

(IVb-1)

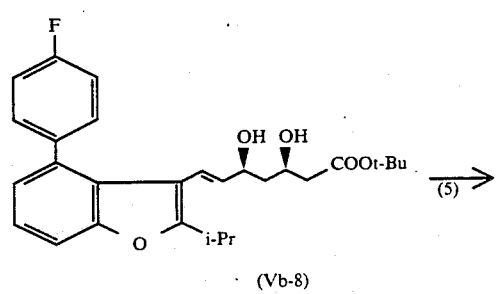

(Vb-8)

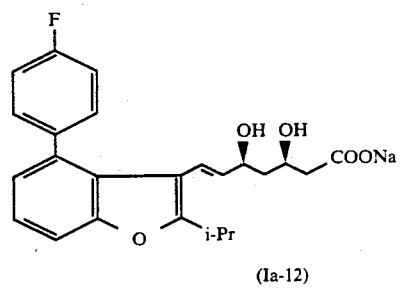

(Ia-12)

(1) A solution of magnesium enolate of optically active compound of ethylacetate (Tetrahedron lett., 28, 1385 (1987), ibid., 25, 5031 (1984)) in 30 ml of THF is cooled to −78° C., and 850 mg of the compound (III-8) obtained in Example 9 is added thereto at −78° C. gradually. The reaction mixture is stirred at the same temperature for 1 hour and mixed with aq.NaHCO₃, and the mixture is brought to room temperature. The suspension is filtered, and the filtrate is extracted with chloroform. The chloroform layer is dried and concentrated under reduced pressure. The residue is subjected to column chromatography of silica gel eluting with hexane/ethyl acetate (4/1) to prepare 1.14 g (Yield: 64%) of the compound (VII-1). mp. 160°–162° C.

(2) To a solution of sodium methoxide in 10 ml of methanol is added the compound (VII-1) obtained above, and the reaction mixture is stirred at room temperature for 1 hour. The mixture is poured into ice-1N.HCl, and the solution is extracted with ether. The ether layer is washed with water, dried, and concentrated under reduced pressure. The residue is subjected to column chromatography of silica gel eluting with hexane/ethyl acetate (4/1) to prepare 789 mg (Yield: 97%) of the compound (VIII-1). mp. 92°–93° C., optical purity: 82% ee (3) To a solution of lithium enolate of tert-butyl acetate in THF is added a solution of 150 mg of the compound (VIII-1) in THF, and the reaction mixture is cooled to −40°– −30° C. and stirred for 2 hours. The solution is cooled to −78° C. and mixed with saturated NH$_4$Cl. The mixture is brought to the room temperature and extracted with ether. The ether layer is washed with water, dried and concentrated under reduced pressure. The residue is subjected to column chromatography of silica gel eluting with hexane/ethyl acetate (3/1) to prepare 125 mg (Yield: 68%) of the compound (IVb-1). mp. 74°–76° C.

(4) The obtained compound (IVb-1) is reacted in the same manner as Example 4(3) to prepare 83 mg (Yield: 89%) of the compound (Vb-8). mp. 72°–74° C.

(5) The compound (Vb-8) is reacted in the same manner as Example 4(4) to prepare 61 mg (Yield: 80%) of the objective compound (Ia-12).

$^1$HNMR (CD$_3$OD)δ: 1.34, 1.35 (each d, 6H, J = 7 Hz); 1.41–1.73 (m, 2H); 2.18–2.41 (m, 2H); 3.39 (sept, 1H, J = 7 Hz); 3.92–4.18 (m, 2H); 5.48 (dd, 1H, J = 6.8, 16 Hz); 5.99 (dd, 1H, J = 1, 16 Hz); 7.03–7.45 (m, 7H).

Anal Calcd. (%) for C$_{24}$H$_{24}$FNaO$_5$.$\frac{1}{2}$H$_2$O.1/6NaOH: C, 64.68; H, 5.58; F, 4.26; Na, 6.02. Found: C, 64.74; H, 5.67; F, 4.38; Na, 6.03.

EXAMPLE 16

Sodium (3R,5S)-(E)-7-[4-(4-fluorophenyl)-2-isopropylbenzofuran-3-yl]-2,2-difluoro-3,5-dihydroxy-6-heptenate (Ia-13)

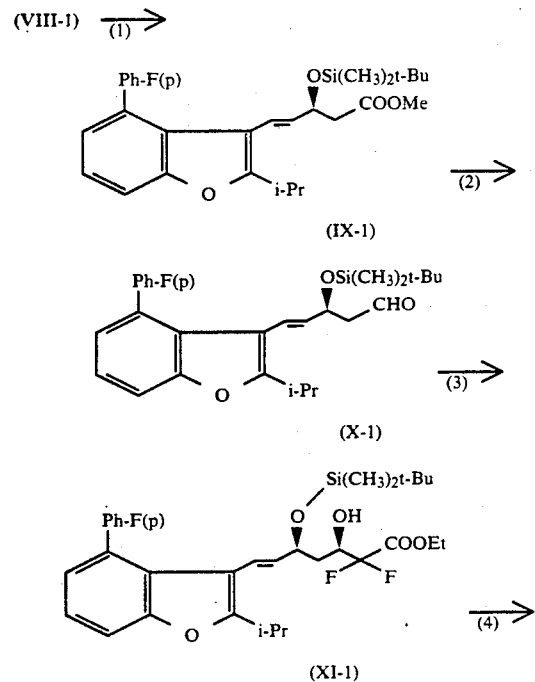

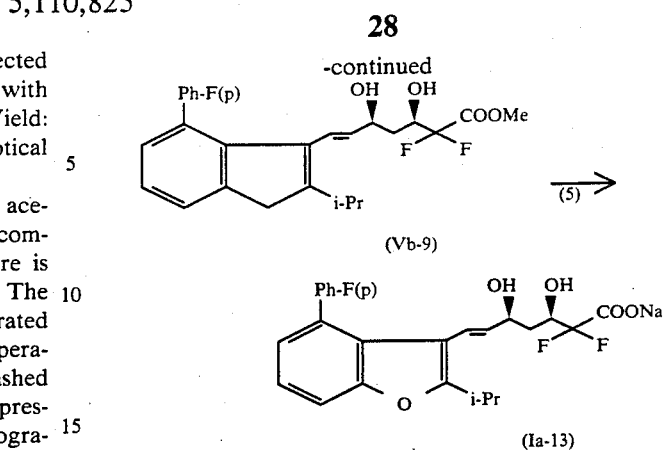

(1) To a solution of 400 mg of the compound (VIII-1) in 10 ml of dry methylene chloride are added 225 mg of 2,6-lutidine and 416 mg of silyl trifluoromethanesulfonate CF$_3$SO$_3$SiMe$_2$C(CH$_3$)$_3$, and the mixture is stirred at room temperature for 1 hour and poured into ice-water. The solution is extracted with methylene chloride, and the methylene chloride layer is washed with water, dried and concentrated. The residue is subjected to column chromatography of silica gel eluting with hexane/ethyl acetate (10/1) to prepare 513 mg (Yield: 99%) of the compound (IX-1).

$^1$HNMR (CDCl$_3$)δ: 0.05 (s, 3H); 0.07 (s, 3H); 0.08 (s, 9H); 1.40, 1.42 (each d, 6H, J = 7 Hz); 2.34–2.56 (m, 2H); 3.37 (sept, 1H, J = 7 Hz); 3.74 (s, 3H); 4.47–4.58 (m, 1H); 5.50 (dd, 1H, J = 6.2, 16 Hz); 6.09 (dd, 1H, J = 1.2, 16 Hz); 7.10–7.52 (m, 7H)

(2) A solution of 508 mg of the compound (IX-1) in 15 ml of hexane/toluene (2/1) is cooled to −78° C., and 1.03 ml of a solution of diisobutylaluminum hydride in hexane is added thereto. The reaction mixture is stirred at the same temperature for 30 minutes and mixed with saturated ammonium chloride. The solution is brought to room temperature and filtered, and the filtrate is extracted with ether. The residue is subjected to column chromatography of silica gel eluting with hexane/ethyl acetate (10/1) to prepare 435 mg. (Yield: 91%) of the compound (X-1).

$^1$HNMR (CDCl$_3$)δ: 0.04 (s, 3H); 0.05 (s, 3H); 0.87 (s, 9H); 1.38, 1.40 (each d, 6H, J = 7 Hz); 2.33–2.59 (m, 2H); 3.32 (sept, 1H, J = 7 Hz); 4.50–4.61 (m, 1H); 5.46 (dd, 1H, J = 6.2,16 Hz); 6.11 (dd, 1H, J = 1.2, 16 Hz); 7.07–7.52 (m, 7H).

(3) A solution of 435 mg of the compound (X-1) in 5 ml of THF is reacted with 284 mg of bromodifluoroacetate under 91 mg of Zn for 15 minutes (Reformatskii reaction). To the reaction mixture is added aqueous ammonium chloride, and the solution is extracted with ether. The ether layer is washed with water, dried and concentrated under reduced pressure. The residue is subjected to column chromatography of silica gel eluting with hexane/ethylacetate (9/1) to prepare 84 mg of (3R,5S) form of the compound (XI-1), 95 mg of (3S,5R) form, and 150 mg of their mixture.

(XI-1):

$^1$HNMR (CDCl$_3$)δ: 0.04, 0.07 (each s, 6H); 0.88 (s, 9H); 1.35–1.47 (m, 9H); 1.72–1.88 (m, 2H); 3.2k–3.46 (m, 2H); 4.10–4.49 (m, 4H); 5.48 (dd, 1H, J = 7, 16 Hz); 6.02 (dd, 1H, J = 1,16 Hz); 7.07–7.50 (m, 7H).

(4) A mixture of 52 mg of the compound (XI-1), 32 mg of acetic acid, and 83 mg of tetrabutylammoniumfluoride is stirred at room temperature for 15 minutes, and further at 50° C. for 3 hours. To the mixture are added 6.2 ml of 0.1N.NaOH and 1 ml of methanol, and the mixture is stirred at 40° C. for 5 minutes. The solution is mixed with acetic acid, and extracted with ether. To the ether layer is added a solution of diazomethane in ether, and then added acetic acid to decompose the excess diazomethane. The reaction mixture is washed with water, dried, and concentrated under reduced pressure. The residue is subjected to column chromatography of silica gel, which was cooled to 0° C., eluting with hexane/ethyl acetate (2/1) to prepare 30.4 mg (Yield: 75%) of the compound (Vb-9). mp. 107°–110° C.

(5) The compound (Vb-9) is reacted in the same manner as Example 4(4) to prepare 25.2 mg (Yield: 98%) of the objective compound (Ia-13).

$^1$HNMR (CD$_3$OD)δ: 1.35, 1.36 (each d, 6H, J=7 Hz); 1.71–1.83 (m, 2H); 3.41 (sept, 1H, J=7 Hz); 3.92–4.20 (m, 2H); 5.53 (dd, 1H, J=7.2 16 Hz); 5.98 (dd, 1H, J=1, 16 Hz); 7.03–7.47 (m, 7H).

EXAMPLE 17

Sodium (3R*,5S*)-(E)-7-[7-(N-acetyl-N-methylamino)-4-(4-fluorophenyl)-2-isopropyl-3-yl]-3,5-dihydroxy-6-heptenate (Ia-14)

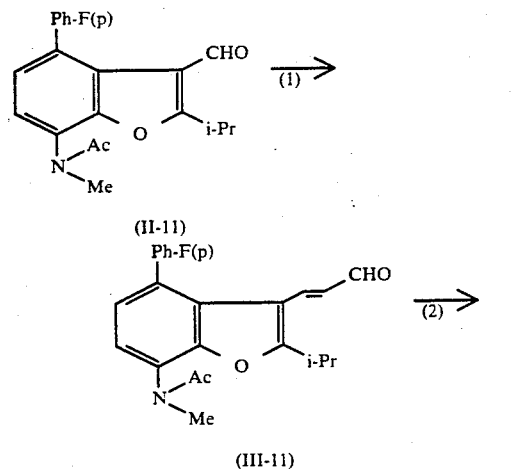

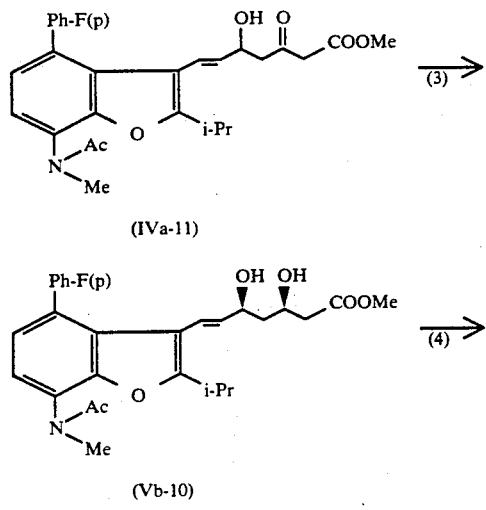

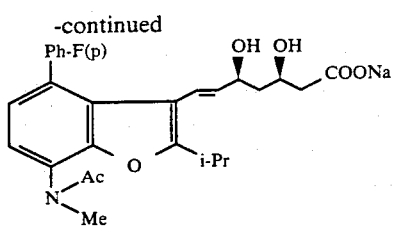

(Ia-14)

As a starting material, 225 mg (0.64 mmol) of the compound (II-11) is reacted in the same manner as Example 4(1)–(4) to prepare 29.9 mg (Yield: 91%) of the objective compound (Ia-14) through the compound (III-11), (IVb-11), and (Vb-10).

(III-11): 149°–152° C.
$^1$HNMR (CDCl$_3$)δ: 1.40 (6H, d, J=6.8 Hz); 1.96 (3H, s); 3.54 (1H, sept); 3.40 (3H, s); 6.00 (1H, dd, J=7.6, 16.2 Hz); 6.97 (1H, d, J=16.2 Hz); 7.09–7.24 (4H, m); 7.30–7.42 (2H, m); 9.24 (1H, d, J=7.6 Hz).

(IVa-11):
$^1$HNMR (CDCl$_3$)δ: 1.34 (6H, d, J=6.8 Hz); 1.94 (3H, s); 2.59 (2H, d, J=6 Hz); 3.27 (1H, sept, J=6.8 Hz); 3.39 (3H, s); 3.48 (2H, s); 3.77 (3H, s); 4.42–4.53 (1H, m); 5.41 (1H, dd, J=5.8,16 Hz); 6.04(1H, dd, J=1,16 Hz); 7.05–7.19 (4H, m); 7.31–7.41 (2H, m).

(Vb-10):
$^1$HNMR (CDCl$_3$)δ: 1.34 (6H, d, J=7 Hz); 1.41–1.63 (2H, m); 1.95 (3H, s); 2.50 (2H, d, J=5.4 Hz); 3.29 (1H, sept, J=7 Hz); 3.39 (3H, s) 3.76 (3H, s); 4.17–4.31 (2H, m); 5.43 (1H, dd, J=6,16 Hz); 6.01 (1H, dd, J=1.4, 16 Hz); 7.05–7.17 (4H, m) 7.31–7.40 (2H, m).

(Ia-14):
$^1$HNMR (CD$_3$OD)δ: 1.347 (3H, d, J=6.8 Hz); 1.352 (3H, d, J=6.8 Hz); 1.41–1.73 (2H, m); 1.89 (3H, s); 2.18–2.41 (2H, m); 3.35 (3H, s); 3.41 (1H, sept, J=6.8 Hz); 3.81–4.06 (1H, m); 4.06–4.19 (1H, m); 5.54 (1H, dd, J=6.8,16 Hz); 5.98 (1H, dd, J=1.1,16 Hz); 7.08–7.29 (4H, m); 7.34–7.47 (2H, m).

m/z: 506 (M+H)+, 528 (M+Na)+, 1011 (2M+H)+, 1033 (2M+Na)+.

EXAMPLE 18

Sodium (3R*,5S*)-(E)-7-[4-(4-fluorophenyl)-2-isopropyl-7-methylamino-3-yl]-3,5-dihydroxy-6-heptenate (Ia-15)

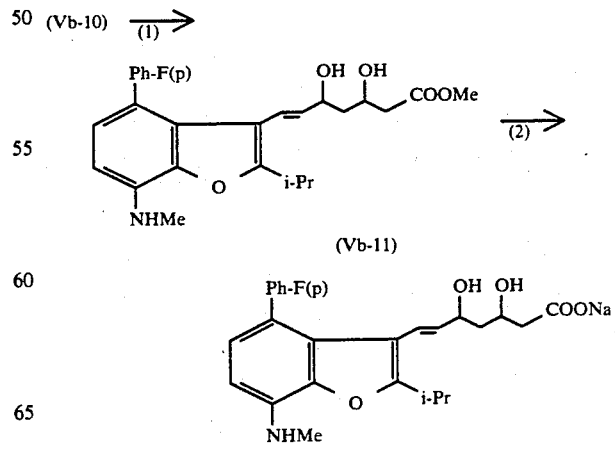

(1) To a solution of 40 mg (0.08 mmol) of the intermediate compound (Vb-10) prepared in Example 17 in 3 ml of DMSO is added 1 ml of 10% NaOH, and the mixture is stirred at 90° C. for 4 hours. After reaction, the mixture is poured into ice-water and extracted with ether. The ether layer is mixed with excess diazomethane to form esters, and remaining diazomethane is decomposed. The ether layer is washed with aqueous NaHCO$_3$ and water, dried over MgSO$_4$ and concentrated under reduced pressure. The residue is subjected to column chromatography of silica gel (ethyl acetate/hexane=1/1) to give 21.9 mg (Yield: 60%) of the compond (Vb-11).

$^1$HNMR (CDCl$_3$)δ: 1.33 (6H, d, J=6.8 Hz); 1.40-1.63 (2H, m); 2.46-2.51 (2H, m); 2.92 (1H, brs, OH); 3.02 (3H, s); 3.27 (1H, sept, J=6.8 Hz); 3.67 (1H, brs, OH); 3.73 (3H, s); 4.17-4.30 (2H, m); 5.37 (1H, dd, J=6.4,16 Hz); 6.06 (1H, dd, J=1.2,16 Hz); 6.55 (1H, d, J=8.2 Hz); 6.94-7.10 (3H, m); 7.26-7.35 (2H, m).

(2) The compound (Vb-11) 21.9 mg (0.05 mmol) is reacted in the same manner as Example 4 (4) to prepare 17.8 mg (Yield: 80%) of the compound (Ia-15).

$^1$HNMR (CD$_3$OD)δ: 1.36 (3H, d, J=7 Hz); 1.37 (3H, d, J=7 Hz); 1.40-1.73 (2H, m); 2.15-2.41 (2H, m); 2.95 (3H, s); 3.38 (1H, sept, J=7 Hz); 3.92-4.03 (1H, m); 4.03-4.17 (1H, m); 5.47 (1H, dd, J=6.8, 16 Hz); 6.03 (1H, dd, J=1,16 Hz); 6.53 (1H, d, J=8 Hz); 6.90 (1H, d, J=8 Hz); 7.04-7.23 (2H, m); 7.27-7.35 (2H, m).

MS m/z: 464 (M+H)+, 486 (M+Na)+, 927 (2M+H)+, 949 (2M+Na)+, 971 (2M+2NaH)+.

EXAMPLE 19

Sodium (3R*,5S*)-(6E,8E)-9-(benzofuran-2-yl)-3,5-dihydroxy-9-(4-fluorophenyl)-8-(1-methyl-1H-tetrazol-5-yl)-6,8-nonadienoate (Ia'-1)

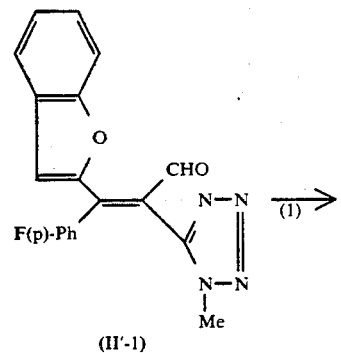

(II'-1)

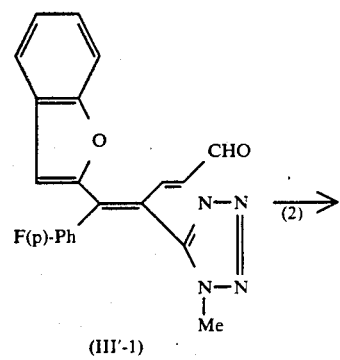

(III'-1)

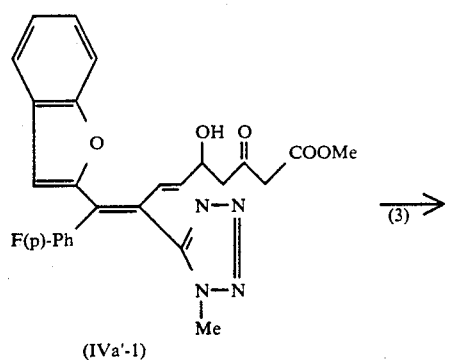

(IVa'-1)

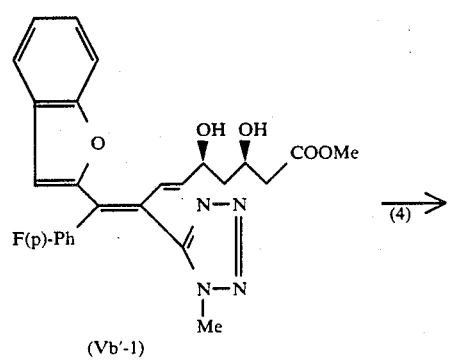

(Vb'-1)

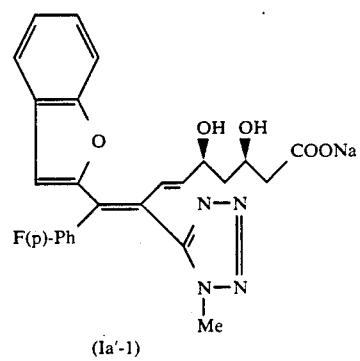

(Ia'-1)

(1) A mixture of 400 mg (1.1 mmol) of the compound (II'-1), 1.37 g (3.4 mmol) of (1,3-dioxolan-2-ylmethyl)-triphenylphosphonium bromide, and 20 ml of dry DMF is heated at 80° C. Further to the reaction mixture is added a solution of lithium-methoxide, which is prepared by reaction with 8.6 ml of n-BuLi (1.58 mmol/l in hexane) and 2.18 ml of absolute methanol, and the mixture is heated at 80° C. for 15 minutes and concentrated to distill DMF. The residue is mixed with 6N.HCl and methanol, and stirred at room temperature for 15 minutes. The reaction mixture is basified with aqueous NaHCO$_3$ and extracted with methylene chloride. The methylene chloride layer is washed with water, dried over Na$_2$SO$_4$, and filtered. The filtrate is concentraed, and the resulting residue is subjected to column chromatography of silica gel eluting with methanol/methylene chloride. The eluate is concentrated and the residue is recrystallized from ethyl acetate/isopropylether to prepare 166 mg (Yield: 39%) of the compound (III'-1) as crystals. mp. 180°-182° C.

IRν (Nujol): 1690, 1599, 1130 cm$^{-1}$.

¹HNMR (CDCl₃)δ: 3.93 (s, 3H); 5.65 (dd, 1H, J=7.5,15 Hz); 6.53 (s, 1H); 7.10~7.55 (m, 9H); 9.47 (d, 1H, J=7.5 Hz).

(2) To a solution of 8 ml of dry THF are added 51 mg (1.3 mmol) of 60%-NaH (oily suspension) and succeedingly added 149 mg (1.3 mmol) of methyl acetoacetate under ice-cooling. After evolution of hydrogen gas, to the reaction mixture is added dropwise 0.82 (1.3 mmol) of n-BuLi (1.58 mol/l in hexane). The reaction mixture is cooled to −78° C., and a solution of 160 mg (0.43 mmol) of the compound (III'-1) in 3.2 ml of dry THF is added thereto. The reaction mixture is stirred at the same temperature for 15 minutes and poured into cooled acetic acid. The solution is basified with aqueous NaHCO₃ and extracted with methylene chloride. The methylene chloride layer is washed with water, dried over Na₂SO₄ and filtered. The filtrate is concentrated and resulting residue is subjected to column chromatography of silica gel eluting with ethyl acetate/n-hexane (1/1) to prepare 120 mg (Yield: 57%) of the compound (IVa'-1) as oily substance.

¹HNMR (CDCl₃)δ: 2.10 (br, 1H); 2.69 (m, 2H); 3.44 (s, 2H); (s, 2H); 3.73 (s, 3H); 3.90 (s, 3H); 4.58 (m, 1H); 5.20 (dd, 1H, J=7.5,15 Hz); 6.28 (s, 1H); 6.52 (d, 1H); 7.02-7.45 (m, 8H).

(3) A mixture of 120 mg (0.25 mmol) of the compound (IVa'-1), 8 ml of dry THF and 4 ml of absolute methanol is cooled to −70° C., and a solution of 0.37 ml (0.37 mmol) of diethylmethoxyborane (1 mol/l in THF) is added thereto. After 15 minutes, the mixture is mixed with 14 mg (0.37 mmol) of NaBH₄, stirred at the same temperature for 0.5 hours, and poured into acetic acid. The solution is basified with aqueous NaHCO₃ and extracted with methylene chloride. The methylene chloride layer is washed with water, dried over Na₂SO₄. The reaction mixture is filtered, and the filtrate is concentrated. The residue is subjected to column chromatography of silica gel eluting with ethyl acetate/n-hexane (1/1) to prepare 77 mg (Yield: 64%) of the compound (Vb'-1) as oily substance.

¹HNMR (CDCl₃)δ: 2.45 (d, 2H, J=7.5); 3.60 (brs, 2H); 3.71 (s, 3H); 3.90 (s, 3H); 4.20 (m, 1H); 4.38 (m, 1H); 5.22 (dd, 1H, J=7.5, 15 Hz); 6.27 (s, 1H) 6.50 (d, 1H, J=15 Hz); 7.05-7.45 (m, 8H).

(4) The compound (Vb'-1) 77 mg (0.16 mmol) is dissolved in 1.5 ml of methanol and 1.5 ml of 0.1N.NaOH. The solution is concentrated on water bath under heating for 5 minutes. The residue is extracted with ether, the aqueous layer is freeze-dried to prepare 55 mg (Yield: 65%) of the objective compound (Ia'-1).

¹HNMR (d₆-DMSO)δ: 1.10-2.05 (m, 4H); 3.60 (m, 1H); 3.93 (m, 3H); 4.12 (m, 1H); 5.15 (dd, 1H, J=7.5,15 Hz); 5.10 (brs,1H); 6.32 (s, 1H); 6.37 (d, 1H, J=15 Hz); 7.05-7.60 (m, 9H).

Anal Calcd. (%) for C₂₅H₂₂FN₄O₅Na.2H₂O: C, 55.97; H, 4.89; N, 10.44. Found: C, 55.97; H, 4.78; N, 10.33.

EXAMPLE 20

Sodium (3R*,5S*)-(6E,8Z)-9-(benzofuran-2-yl)-3,5-dihydroxy-9-(4-fluorophenyl)-8-(1-methyl-1H-tetrazol-5-yl)-6,8-nonadienoate (Ia'-2)

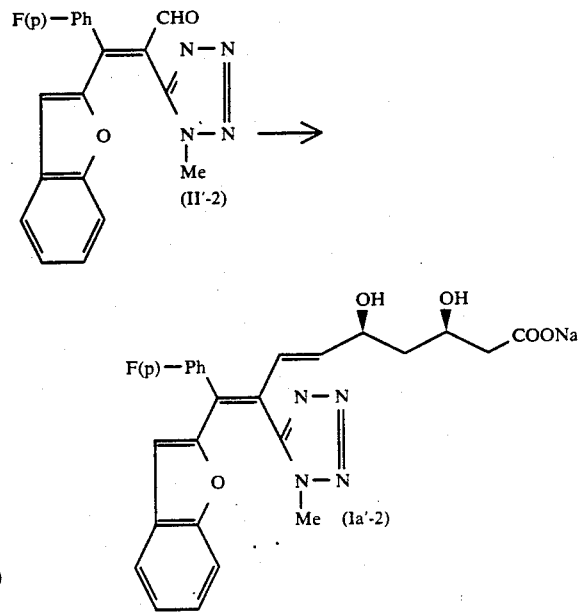

As a starting material the compound (II'-2) is reacted in the same manner as Example 19(1)–(4) to prepare the objective compound (Ia'-2) (Yield: 70%), which is the isomer of the compound (Ia'-1), through (2E,4Z)-5-(benzofuran-2-yl)-5-(4-fluorophenyl)-4-(1-methyl-1H-tetrazol-5-yl)-2,4-pentadienol (III'-2), methyl (6E,8Z)-9-(benzofuran-2-yl)-9-(4-fluorophenyl)-5-hydroxy-8-(1-methyl-1H-tetrazol-5-yl)-3-oxo-6,8-nonadienoate (IVa'-2), and methyl (3R*,5S*)-(6E,8Z)-9-(benzofuran-2-yl)-3,5-dihydroxy-9-(4-fluorophenyl)-8-(1-methyl-1H-tetrazol-5-yl)-6,8-nonadienoate (Vb'-2).

(III'-2): mp. 178°–180° C.

¹HNMR (CDCl₃)δ: 3.93 (s, 3H); 6.65 (dd, 1H, J=7.5,15 Hz); 6.54 (s, 1H); 7.10-7.50 (m, 9H); 9.46 (d, 1H, J=7.5 Hz).

(IVa'-2):

IRν (Nujol): 1738, 1710 cm⁻¹.

¹HNMR (CDCl₃)δ: 1.60 (brs, 1H); 2.70 (m, 2H); 3.50 (s, 2H); 3.73 (s, 3H); 3.90 (s, 3H); 4.58 (m, 1H); 5.20 (dd, 1H, J=7.5, 15 Hz); 6.28 (s, 1H); 6.52 (d, 1H, J=15 Hz); 7.00-7.50 (m, 8H).

(Vb'-2):

¹HNMR (CDCl₃)δ: 1.65 (brs, 1H); 2.45 (m, 2H); 3.50 (br, 1H); 3.72 (s, 3H); 3.90 (s, 3H); 4.20 (m, 1H); 4.39 (s, 3H); 5.20 (dd, 1H, J=7.5,15 Hz); 6.27 (s, 1H); 6.52 (d, 1H, J=15 Hz); 7.00-7.50 (m, 8H).

(Ia'-2):

¹HNMR (d₆DMSO)δ: 1.20-2.05 (m, 4H); 3.60 (m, 1H); 3.92 (s, 3H); 4.10 (m, 1H); 5.10 (brs, 1H); 5.12 (dd, H, J=7.5,15 Hz); 6.32 (s, 1H); 6.35 (d, 1H, J=15 Hz); 7.05-7.80 (m, 9H).

Anal Calcd. (%) for C₂₅H₂₂FN₄O₅Na.6/5H₂O: C, 57.51; H, 4.71; N, 10.73. Found: C, 57.35; H, 4.85; N, 10.66.

REFERENCE EXAMPLE 1

Synthesis of the Compound (II-1)

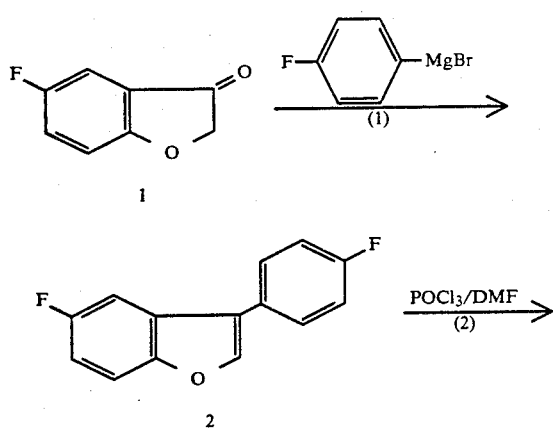

REFERENCE EXAMPLE 2-4

Each starting material is reacted in the same manner as Reference Example 1 to prepare the compound (II-2), (II-3), and (II-10).

Each material, agent, and physical constant are shown in the table 1.

te/n-hexane (1/5 v/v) to prepare 2.7 g (Yield: 47%) of the compound 2 as yellow oily substance.

(2) To a mixture of 9.07 g of $POCl_3$ and 4.29 g of dry DMF is added 2.7 g of the compound 2, and the reaction mixture is reacted at 80° C. for 3 hours. The mixture is poured into aq. $NaHCO_3$, and the solution is extracted with ethyl acetate. The organic layer is washed with water, dried and concentrated. The residue is subjected to column chromatography of silica gel eluting with methylene chloride to prepare 1.57 g (Yield: 52%) of the objective compound (II-1). mp. 181°-182° C.

IR$\nu$ (Nujol) cm$^{-1}$: 1680, 1230.

$^1$HNMR (CDCl$_3$)$\delta$: 7.20-7.80 (m, 7H); 9.89 (s, 1H).

TABLE 1

| Reference No. | Material | Reagent g (mmol) | product | $^1$HNMR (CDCl$_3$) $\delta$ | IR cm$^{-1}$ |
|---|---|---|---|---|---|
| 2 | (benzofuranone with i-Pr) | F-C6H4-MgBr, 7.83 g (44.6 mmol) | (II-2) | 1.42(d, 6H, J=7.0Hz); 3.62 (sept, 1H); 7.23~7.66(m, 7H); 9.87(s, 1H) | (Nujol) 2060, 1668, 747 |
| 3 | (Cl, Me, i-Pr benzofuranone) | F-C6H4-MgBr, 7.85 g (44.7 mmol) | (II-3) | 1.36(d, 6H, J=7.0Hz); 2.12 (s, 3H); 7.15~7.47(m, 5H) | |
| 4 | (i-Pr benzofuranone) | F-C6H4-MgBr, 10.73 g (56.7 mmol) | (II-10) | 1.43(d, 6H, J=7.0Hz); 2.39 (d, 3H); 3.62(sept, 1H); 7.18~7.55(m, 6H); 9.85(s, 1H) | |

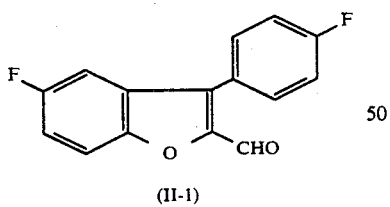

(II-1)

(1) To a solution of 7.8 g of 3(2H)-5-fluorobenzofuranone 1 in 39 ml of dry THF is added a solution of 4-fluorophenyl-magnesium bromide in THF at room temperature. The reaction mixture is reacted at room temperature for 10 minutes, and ice-water is added thereto. The solution is acidified with 6N.HCl and extracted with ether. The ether layer is washed with water, dried and concentrated. To the residue are added 50 ml of toluene and 300 mg of p-toluenesulfonic acid, and the mixture is heated at 90° C. for 15 minutes. After cooling, the solution is washed with aq. $NaHCO_3$ to separate the organic layer, and the obtained organic layer is dried and concentrated. The residue is subjected to column chromatography of silica gel eluting with ethyl aceta-

REFERENCE EXAMPLE 5

Synthesis of the Compound (II-5)

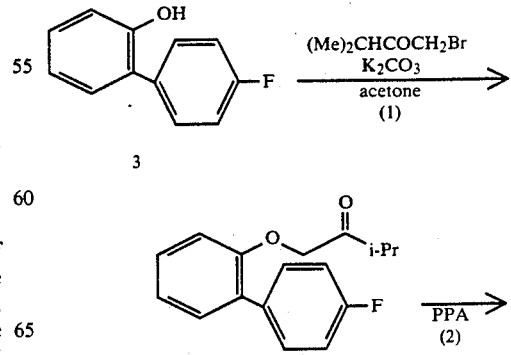

-continued

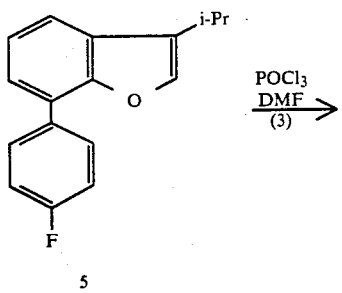

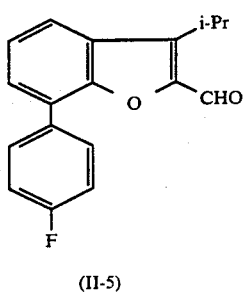

(II-5)

(1) To 1.0 g (5.31 mmol) of the compound 3 are added 10 ml of dry acetone, 1.1 g of K₂CO₃, and 1.05 g of 1-bromo-3-methyl-2-buthanone, and the mixture is refluxed under heating for 1 hour. To the reaction mixture is added ice-water, and the solution is extracted with methylene chloride. The organic layer is washed with water, dried and concentrated. The residue is subjected to column chromatography of silica gel eluting with acetone/hexane (1/10) to prepare 1.2 g (Yield: 83.3%) of the compound 4.

¹HNMR (CDCl₃): 1.01 (d, 6H, J=7.0 Hz); 2.77 (sept, 1H);4.55 (s, 2H); 6.76–6.80 (m, 1H); 7.02–7.11 (m, 3H); 7.22–7.30 (m, 2H); 7.45–7.58 (m, 2H).

(2) To 1 g (3.67 mmol) of the compound 4 are added 4 g of PPA (polyphosphoric acid) and 20 ml of dry xylene, and the mixture is stirred under heating for 15 hours. The reaction mixture is extracted with ehter, the xylene layer is washed with water, dried and concentrated. The residue is subjected to column chromatography of silica gel eluting with hexane to prepare 283 mg (Yield: 29%) of the compound 5.

¹HNMR (CDCl₃): 1.36 (d, 6H, J=7.0 Hz); 3.10 (sept, 1H);6.85–7.83 (m, 8H).

(3) The compound 5 280 mg (1.1 mmol) is reacted in the same manner as Reference Example 1 (2) to prepare 141 mg (Yield: 45%) of the objective compound (II-5).

NMR (CDCl₃): 1.48 (d, 6H, J=7.0 Hz); 3.82 (sept, 1H);7.12–7.22 (m, 2H); 7.30–7.38 (m, 1H); 7.54–7.60 (m, 1H); 7.75–7.82 (m, 3H); 10.05 (s, 1H).

REFERENCE EXAMPLE 6

Synthesis of the Compound (II-6)

(1) To 3 g of carvacrol are added 30 ml of dry acetone, 3.3 g of K₂CO₃, and 5.54 g of α-bromo-4′-fluoro-3′-methylacetophenone, and the mixture is reacted in the same manner as Reference Example 5 (1) to prepare 4 g of ketone compound.

(2) To 3 g of ketone compound obtained above is added 45 g of PPA, and the mixture is heated at 140° C. for 17 hours and extracted with ether. The organic layer is treated in the same manner as Reference Example 5 (2) to prepare 2.80 g of 4-isopropyl-2-(4-fluoro-3-methylphenyl)-7-methylbenzofuran.

(3) To 10.9 g of dry DMF is added 22.8 g of POCl₃ under ice-cooling, and the mixture is stirred for 15 minutes. To the reaction mixture is added 2.8 g of the compound obtained above, and the mixture is stirred under heating at 130° C. for 2 hours. The reaction mixture is cooled and poured into ice-water. The solution is extracted with ether, and the ether layer is washed with water, dried and concentrated. The residue is subjected to column chromatograpy of silica gel eluting with hexane to prepare the objective compound (II-6).

¹HNMR (CDCl₃)δ: 1.20 (d, 6H, J=7.0 Hz); 2.23 (s, 3H); 2.54 (d, 3H, J=1 Hz); 4.19 (sept, 1H); 7.12–7.25 (m, 4H); 7.58–7.65 (m, 2H); 10.16 (s, 1H).

REFERENCE EXAMPLE 7

Synthesis of the Compound (II-7)

(1) A mixture of 500 mg of carvacrol, 516 mg of diisopropylehtylamine, and 795 mg of α-bromo-4′-fluoroacetophenone in dry acetonitrile is refluxed for 15 hours and treated in the same manner as Reference Example 5 (1) to prepare 4 g of ketone compound.

(2) To 2.4 g of ketone compound obtained above is added 29 g of PPA, and the mixture is heated at 140° C. for 21 hours and extracted with ether. The organic layer is treated in the same manner as Reference Example 5 (2) to 1.66 g of 4-isopropyl-2-(4-fluorophenyl)-7-methylbenzofuran.

(3) 1.3 g of the compound obtained above, 3.54 g of dry DMF, and 7.43 g of POC₃ are treated in the same manner as Reference Example 6 (3) to prepare 492 mg of the objective compound (II-7). mp. 86°–88° C.

¹HNMR (CDCl₃)δ: 1.30 (d, 6H, J=6.8 Hz); 2.53 (s, 3H); 4.15 (sept, 1H, J=6.8 Hz); 7.07–7.29 (m, 4H); 7.78–7.85 (m, 2H).

REFERENCE EXAMPLE 8

Synthesis of the Compound (II-4)

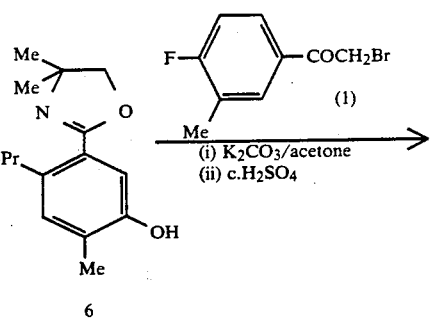

6

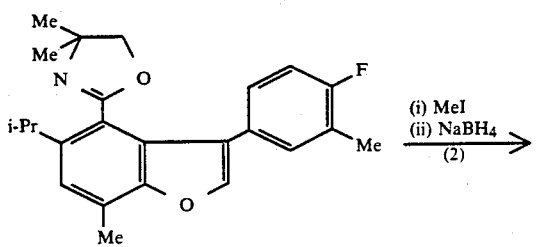

7

-continued

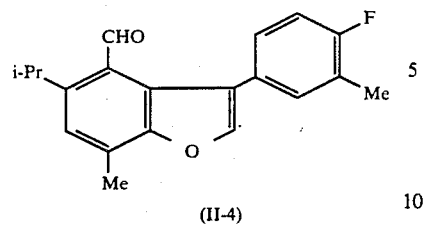

(II-4)

(1) To a mixture of 1 g (4 mmol) of the compound 6, 1.68 g (12.1 mmol) of K₂CO₃, and 20 ml of dry acetone is added 1.40 g (6 mmol) of 4-fluoro-3-methylphenacyl bromide, and the reaction mixture is refluxed for 1.5 hours and concentrated. To the residue is added ice-water, and the solution is extracted with methylene chloride. The organic layer is washed with water, dried and concentrated. The residue is subjected to column chromatography of silica gel eluting with ethyl acetate/n-hexane (1/5). The obtained compound 1.48 g is mixed with 12 ml of c.H₂SO₄ and heated at 75° C. for 45 minutes. After cooling, the reaction mixture is poured into aq.NaHCO₃, and the solution is extracted with ethyl acetate. The organic layer is washed with water, dried and concentrated. The residue is subjected to column chromatography of silica gel eluting with ethyl acetate/n-hexane (1/10) to prepare 340 mg (Yield: 30%) of the compound 7.

IRν (Nujol) cm⁻¹: 1630, 1230, 1190.

(2) To 6 ml of methyl iodide is added 340 mg (0.7 mmol) of the compound 7, and the reaction mixture is refluxed for 7 hours and concentrated. To the residue is added ether to filter off impurity, and 375 mg of resulting crystals are dissolved in 10 ml of ethanol. Then to the reaction mixture is added 27 mg of NaBH₄, and the mixture is stirred at room temperature for 1 hour and acidified with 6N.HCl. The solution is stirred at room temperature for 1 hour again and extracted with ethyl acetate. The organic layer is washed with water, dried and concentrated. The residue is subjected to column chromatography of silica gel eluting with methylene chloride to prepare 80 mg (Yield: 3.6%) of the objective compound (II-4).

IRν (Nujol) cm⁻¹: 1665.

REFERENCE EXAMPLE 9

Synthesis of the Compound (II-8)

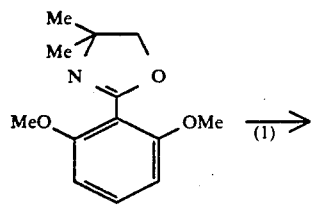

8

-continued

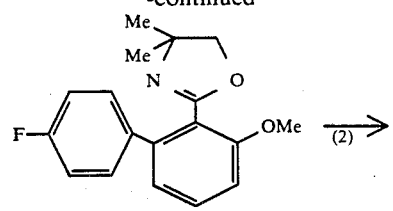

9

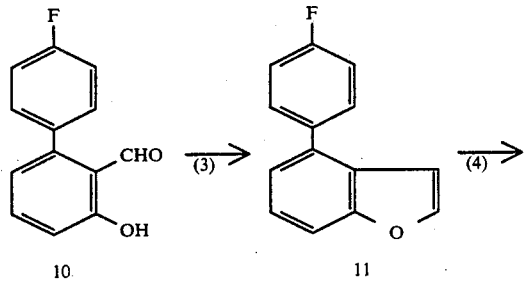

10

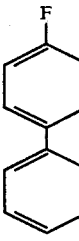

11

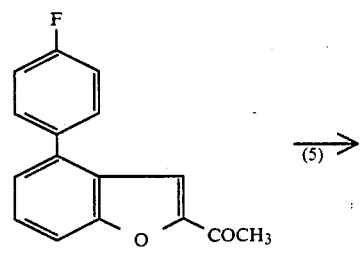

12

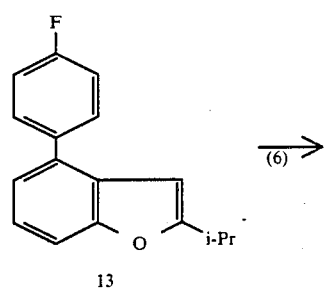

13

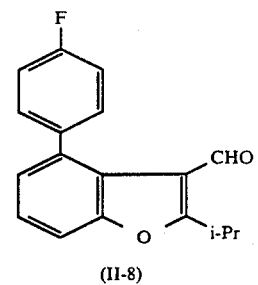

(II-8)

(1) To a solution of 7 g of oxazoline compound 8 in dry THF is added a solution of p-fluorophenylmagnesium bromide in 100 ml of THF at room temperature, and the solution is stirred at the same temperature for 17 hours and further refluxed under heating for 5 hours. The reaction mixture is cooled to room temperature, and saturated ammonium chloride is added thereto. The resulting inorganic substance is filtered off, and the filtrate is concentrated under reduced pressure. To the residue is added toluene and the mixture is concentrated under reduced pressure. The residue is subjected to column chromatography of silica gel eluting with hexane/ethyl acetate (1/1) to prepare 6.27 g (Yield: 70%) of the biphenyl compound 9. mp. 95°-97° C.

(2) A solution of 4.2 g of the obtained compound 9 in 84 ml of 47% hydrobromic acid is stirred under heating at 130° C. for 15 hours. To the solution is added ice, and the aqueous layer is extracted with ether, neutralized with potassium carbonate, and extracted with ether again. The ether layer is washed with water, dried and concentrated under reduced pressure to give 3.32 g of phenol compound (mp. 95°-101° C.). To a suspension of 4 g of the obtained phenol compound, 500 mg of Adogen ® 464 (ammonium chloride) in 20 ml of methylene chloride, and 1.16 g of 97% of sodium hydroxide is added 4.52 g of chloromethyl methyl ether with stirring under cooling. The methylene chloride layer is washed with water, dried and concentrated under reduced pressure. The residue is subjected to column chromatography of silica gel eluting with hexane/ethyl acetate (2/1) to prepare 3.78 g of methoxymethyl ether compound. The compound is treated in the same manner as Reference Example 8 (2) to prepare 820 mg of the compound 10. mp. 68°-69° C.

$^1$HNMR (CDCl$_3$)δ: 6.81-7.57 (m, 7H); 9.81 (s, 1H); 11.89 (s, 1H).

(3) To a solution of dimethylsulfoxonium methiride in 20 ml of DMSO is added 710 mg of the compound 10, and the solution is stirred at room temperature for 30 minutes. The reaction mixture is mixed with ice and extracted with ether. The ether layer is washed with water, dried and concentrated under reduced pressure. To the residue are added 10 mg of p-toluenesulfonic acid and 30 ml of toluene, and the mixture is refluxed under heating for 2 hours. The reaction mixture is poured into saturated NaHCO$_3$ and the solution is extracted with ether. The ether layer is washed with water, dried and concentrated under reduced pressure to prepare 696 mg (Yield: 91%) of the compound 11.

$^1$HNMR (CDCl$_3$)δ: 6.84-6.91 (m, 1H); 7.09-7.68 (m, 8H).

(4) A solution of 680 mg of the obtained compound 11 in 5 ml of dry THF is cooled to −78° C., and a solution of n-butyllithium in hexane is added thereto under stirring. After stirring at the same temperature for 1 hour, to the reaction mixture is added 522 mg of chlorotrimethylsilane at −70° C. The mixture is brought to room temperature gradually, the resulting inorganic substance is filtered off by adding n-pentane. The filtrate is concentrated under reduced pressure to prepare 938 mg of crude sillyl compound (mp. 107°-111° C.). To a solution of 930 mg of the obtained sillyl compound and acetyl chloride in dry methylene chloride is added 842 mg of titanium tetrachloride under stirring at −78° C., and the mixture is stirred at the same temperature for 15 minutes. The reaction mixture is mixed with water, brought to room temperature and extracted with methylene chloride. The methylene chloride layer is washed with water, dried and concentrated under reduced pressure. The residue is subjected to column chromatography of silica gel eluting with hexane/ethyl acetate (4/1) to prepare 615 mg (Yield: 75%) of the compound 12. mp. 136°-138° C.

(5) The obtained compound 12 is mixed with a solution of triphenylphosphoniummethiride in dry ether and stirred at room temperature for 1 hour. The mixture is filtered, and the filtrate is concentrated under reduced pressure. The residue is subjected to column chromatography of silica gel eluting with hexane/ethyl acetate (10/1). The obtained olefin compound 425 mg is subjected to catalytic reduction under a solution of 45 mg of platinum oxide in methanol. The reaction mixture is filtered, and the filtrate is concentrated to distill methanol. The resulting residue is subjected to column chromatography of silica gel eluting with hexane to prepare 295 mg (Yield: 69%) of the compound 13.

$^1$HNMR (CDCl$_3$)δ: 1.35 (d, 6H, J=7.0 Hz); 3.09 (sept, 1H, J=7.0 Hz); 6.48 (s, 1H); 7.10-7.34 (m, 4H); 7.37-7.44 (m, 1H); 7.53-7.63 (m, 2H).

(6) The compound 13 295 mg is reacted in the same manner as Reference Example 6 (3) to prepare 93 mg (Yield: 30%) of the compound (II-8).

$^1$HHMR (CDCl$_3$)δ: 1.37 (d, 6H, J=6.8 Hz); 3.90 (sept, 1H, J=6.8 Hz); 7.07-7.21 (m, 3H); 7.30-7.53 (m, 4H).

REFERENCE EXAMPLE 10

Synthesis of the Compound (II-9)

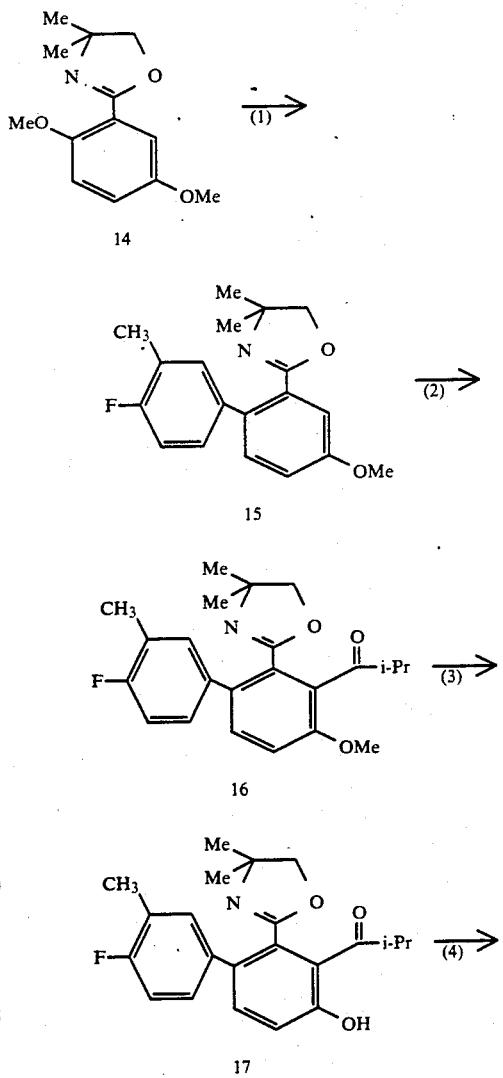

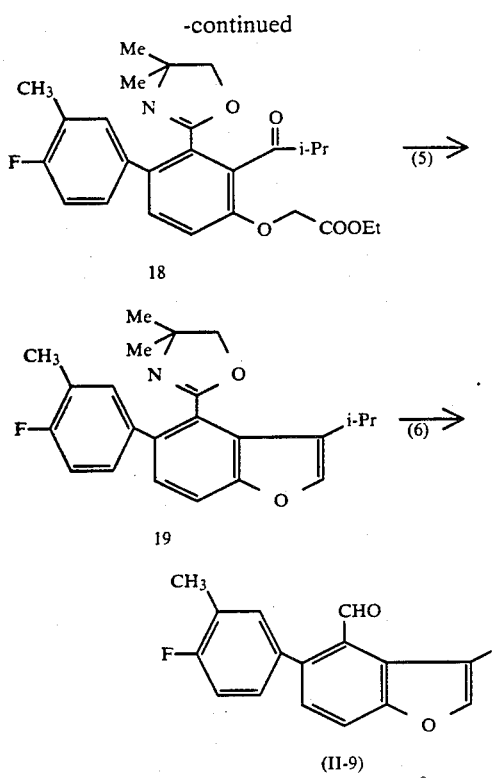

(1) To a solution of 5 g of the compound 14 in 50 ml of dry THF is added a solution of 4-fluoro-3-methylphenylmagnesiumbromide in 100 ml of THF at room temperature, and the mixture is stirred at the same temperature for 88 hours. To the reaction mixture is added a solution of saturated ammonium chloride to filter off the resulting inorganic substance. The resulting filtrate is concentrated under reduced pressure, and the residue is mixed with toluene and concentrated under reduced pressure. The residue is subjected to column chromatography of silica gel eluting with hexane/ethyl acetate (1/1) to prepare 6.49 g of the compound 15.

(2) A solution of 4.68 g of the compound 15 in 47 ml of dry ether is cooled to −78° C., a solution of n-butyllithium in THF is added thereto under −65° C. Then the reaction mixture is stirred at 0° C. for 75 minutes and cooled to −70° C. again, and mixed with 1.88 g of isobutylaldehyde. The reaction mixture is brought to room temperature gradually, mixed with saturated ammonium chloride, and extracted with ether. The ether layer is washed with water, dried and concentrated under reduced pressure. The residue is subjected to column chromatography of silica gel eluting with hexane/ethyl acetate (4/1) to prepare 5.15 g of alcohol compound. A solution of 4.4 g of obtained alcohol compound in 44 ml of dry methylene chloride is mixed with 5.8 g of Des-Martin agent (J. Org. Chem. 48, 4155 (1983)), and stirred at room temperature for 30 minutes. The reaction mixture is mixed with a solution of 0.26M sodium thiosulfate in 360 ml of saturated NaHCO$_3$ and extracted with methylene chloride. The methylene chloride layer is washed with saturated NaHCO$_3$ and water, dried and concentrated under reduced pressure. The residue is subjected to column chromatography of silica gel eluting with hexane/ethyl acetate (2/1) to prepare 1.68 g of ketone compound 16 (mp. 148°–152° C.).

(3) A solution of 1.65 g of the compound 16 in dry methylene chloride is cooled to −60° C., mixed with a solution of boron tribromide in 16 ml of methylene chloride, and the solution is stirred at room temperature for 85 minutes. The reaction mixture is poured into ice-saturated NaHCO$_3$, and the solution is extracted with methylene chloride. The methylene chloride layer is washed with water and concentrated under reduced pressure. The residue is mixed with 5%.NaOH, and washed with ether. The aqueous layer is acidified with d.HCl, neutralized with saturated NaHCO$_3$ and extracted with ether. The ether layer is washed with water, dried and concentrated under reduced pressure. The residue is subjected to column chromatography of silica gel eluting with hexane/ethyl acetate (3/2) to prepare 599 mg (Yield: 38%) of the compound 17 (mp. 180°–184° C.).

(4) A suspension of 460 mg of the compound 17, 225 mg of potassium carbonate, 248 mg of bromo ethylacetate ester, and 10 ml of ethylmethylketone is refluxed under heating for 100 minutes. The reaction mixture is poured into ice-water, and the resulting crystals are filtered off. The obtained crystals are dissolved in methylene chloride, dried and concentrated under reduced pressure to prepare 532 mg of the compound 18.

$^1$HNMR (CDCl$_3$)δ: 1.16 (s, 6H); 1.23 (d, 6H, J=7 Hz); 1.30 (t, 3H, J=7 Hz); 2.27 (d, 3H, J=2 Hz); 3.28 (1H, J=7 Hz); 3.78 (s, 2H); 4.27 (q, 2H, J=7 Hz); 4.68 (s, 2H); 6.87–7.32 (m, 5H).

(5) To a solution of 532 mg of the compound 18 in 30 ml of dry methanol is added 14 ml of 0.1N.NaOH, and the mixture is stirred at room temperature for 30 minutes and concentrated under reduced pressure. The residue is dissolved in water, and neutralized with d.HCl. The resulting crystals are filtered off to obtain the carboxylic acid derivative. A mixture of its derivative, 1.05 g of sodium acetate, and 1.6 g of acetic anhydride is stirred at 150° C. for 70 minutes under stirring. The reaction mixture is mixed with ice, neutralized with NaHCO$_3$, and extracted with ether. The ether layer is washed with water, dried and concentrated under reduced pressure. The residue is subjected to column chromatography of silica gel eluting with hexane/ethyl acetate (4/1) to prepare 325 mg (Yield: 71%) of the compound 19.

(6) The compound 19 414 mg is reacted in the same manner as Reference Example 8 (2) to prepare 55 mg (Yield: 18%) of the compound (II-9).

$^1$HNMR (CDCl$_3$)δ: 1.25 (d, 6H, J=6.6 Hz); 2.35 (d, 3H, J=2 Hz); 3.65 (sept, 1H, J=6.6 Hz); 7.03–7.71 (m, 6H); 10.08 (s, 1H).

IR (CHCl$_3$) cm$^{-1}$: 1685.

REFERENCE EXAMPLE 11

Synthesis of the Compound (II-11)

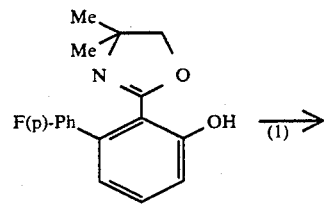

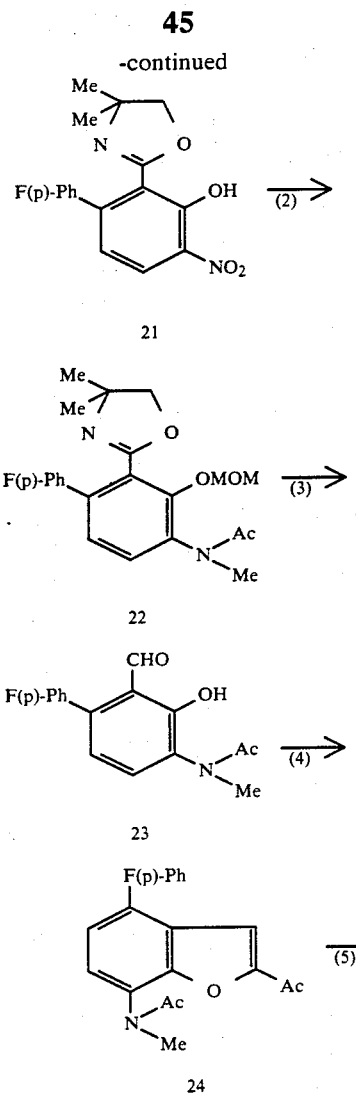

(1) To a solution of 15 g (53 mmol) of the compound 20 in 150 ml of acetic acid is added 8.07 ml of 60% nitric acid, and the mixture is stirred at room temperature for 3 hours. The reaction mixture is stirred at room temperature for 3 hours. The reaction mixture is poured into ice-water and the resulting crystals are collected. The crystals are dissolved in methylene chloride, dried over MgSO4 and concentrated under reduced pressure. The residue is subjected to column chromatography of silica gel eluting with hexane/ethyl acetate (2/1) to prepare 6.9 g (Yield: 40%) of the compound 21. mp. 123°–125° C.

$^1$HNMR (CDCl$_3$)δ: 1.34 (6H, s); 3.87 (7H, s); 6.83 (1H, d, J=8.6 Hz); 7.02–7.17 (2H, m); 7.22–7.36 (2H, m); 8.09 (1H, d, J=8.6 Hz)

(2) To a solution of 3.0 g (9.1 mmol) of the compound 21 in 50 ml of anhydrous DMF is added 436 mg of 60% NaH under ice-cooling, and the mixture is stirred for 5 minutes. To the mixture is added 805 mg of chloromethyl methyl ether, and the mixture is stirred at room temperature for 30 minutes. The reaction mixture is poured into ice-water and extracted with ether. The ether layer is washed with water, dried over MgSO4 and concentrated. The residue is washed with petroleum ether and subjected to catalytic reduction under platinum catalyst (prepared by the hydrogenation of the methanol suspension of oxidative platinum) under hydrogen atmosphere. After reaction, the catalyst are filtered off, and the filtrate is concentrated under reduced pressure. The residue is mixed with 30 ml of acetic anhydride and stirred at room temperature. The reaction mixture is poured into ice-water, and the solution is neutralized with K2CO3 and extracted with ether. The ether layer is washed with water, dried over MgSO4 and concentrated. The residue is subjected to column chromatography of silica gel eluting with ethyl acetate. To a suspension of 299 mg of NaH in 50 ml of anhydrous DMF is added the purified product under ice-cooling. The reaction mixture is stirred at room temperature for 15 minutes, mixed with 1.76 g of methyl iodide and stirred at room temperature for 30 minutes. The reaction mixture is poured into ice-water and extracted with ether. The ether layer is washed with water, dried over MgSO4 and concentrated to prepare 4.14 g (Yield: 100%) of the compound 22.

$^1$HNMR (CDCl$_3$)δ: 1.18 (3H, s); 1.20 (3H, s); 1.97 (3H, s); 3.28 (3H, s); 3.50 (3H, s); 3.90 (2H, s); 5.07 (1H, d, J=6 Hz); 5.10 (1H, d, J=6 Hz); 7.03–7.45 (6H, m).

(3) The compound 22 4.14 g (10.3 mmol) is dissolved in 20 ml of methyl iodide and kept at room temperature for 60 hours to collect the resulting crystals. To a solution of the crystals in 150 ml of ethanol is added 394 mg of sodium borohydride under ice-cooling, and the mixture is stirred at the same temperature for 45 minutes. The mixture is poured into a mixture of d-HCl and ice, and the solution is extracted with ether. The ether layer is washed with water, dried over MgSO4, and concentrated. To the residue are added 50 ml of dioxane and 50 ml of 10%-H2SO4, and the mixture is stirred at 90° C. for 30 minutes and mixed with ice. The mixture is extracted with ether, and the ether layer is washed with water, dried over MgSO4 and concentrated. The residue is dissolved in 20 ml of acetonitrile, and the solution is mixed with 0.2 ml of DBU, refluxed for 30 minutes under heating and concentrated. The residue is subjected to column chromatography of silica gel to prepare 1.08 g (Yield: 36%) of the compound 23. mp. 95°–97° C.

$^1$HNMR (CDCl$_3$)δ: 1.93 (3H, s); 3.25 (3H, s); 6.93 (1H, d, J=8 Hz); 7.08–7.42 (4H, m); 7.46 (1H, d, J=8 Hz); 9.84 (1H, s).

(4) To a solution of 1.05 g (3.7 mmol) of the compound 23 in 10 ml of anhydrous DMF are added 175 mg of 60% NaH and 406 mg of chloroacetone, and the mixture is stirred at 50° C. for 1 hour. The reaction mixture is poured into ice-water and extracted with ether. The ether layer is washed with water, dried over MgSO4 and concentrated. The residue is dissolved in 20 ml of acetonitrile and mixed with 20 ml of DBU. The mixture is refluxed under heating for 30 minutes and concentrated. The residue is subjected to column chromatography of silica gel to prepare 721 mg (Yield: 61%) of the compound 24. mp. 178°–180° C.

$^1$HNMR (CDCl$_3$)δ: 1.96 (3H, s); 2.63 (3H, s); 3.42 (3H, s); 7.16–7.28 (H, m); 7.38 (2H, s); 7.53–7.64 (2H, m); 7.66 (1H, s).

IR (CDCl$_3$)ν: 1676, 1651 cm$^{-1}$.

(5) The compound 24 720 mg (2.21 mmol) is reacted in the same manner as Reference Example 9(5)–(6) to prepare 234 mg (Yield: 70%) of the compound (II-11). mp. 132°–141° C.

$^1$HNMR (CDCl$_3$)δ: 1.37 (6H, d, J=7 Hz); 1.95 (3H, s); 3.40 (3H, s); 3.90 (1H, sept, J=7 Hz); 7.10–7.25 (4H, m); 7.39–7.48 (2H, m); 9.62 (1H, s).

REFERENCE EXAMPLE 12

The Compound (II'-1) (E) and the Compound (II'-2) (Z)

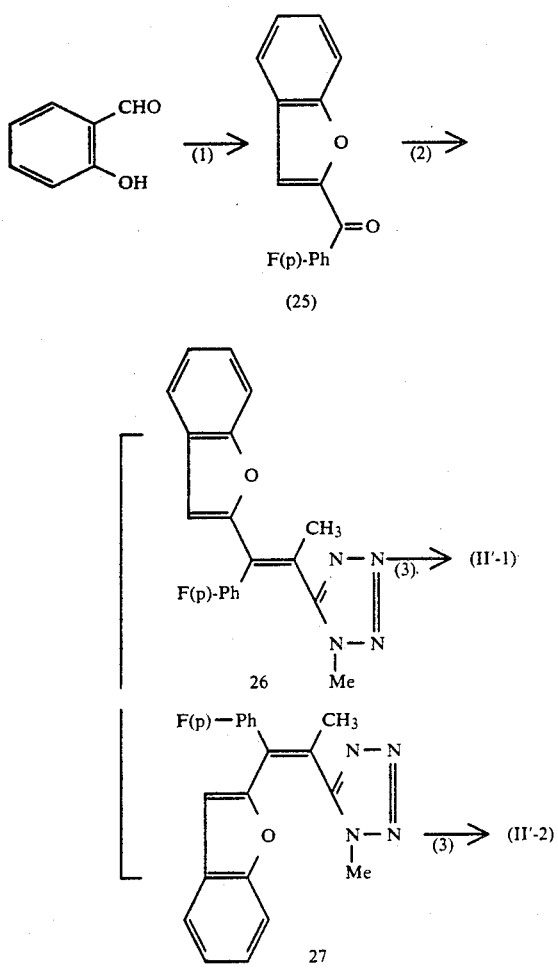

(1) A mixture of 5 g (40.9 mmol) of salicylaldehyde, 7.0 g (40.6 mmol) of 4-chlorophenacyl chloride, 5.7 g (41.2 mmol) of K₂CO₃, and 2 g of potassium iodide is mixed with 20 ml of ethanol and brought gradually to 100° C. and heated for 1.5 hours. After cooling, the mixture is poured into ice-water. The solution is mixed with 10% NaOH, the resulting crystals are collected, washed with water, and dried. The residue is subjected to column chromatography of silica gel eluting with methylene chloride. The residue is treated with isopropyl ether/n-hexane to prepare 7.8 g (Yield: 80%) of the compound 25. mp. 134°–135° C.

IR (Nujol): 1650, 1600, 1221 cm⁻¹.

¹HNMR (CDCl₃)δ: 7.15–7.75 (m, 7H); 8.10–8.18 (m, 2H).

(2) A solution of 2.1 g (18.7 mmol) of 5-ethyl-1-methyltetrazole in 20 ml of dry THF is cooled to −78° C., and a solution of 11.9 ml of n-BuLi is added dropwise thereto. To the mixture is added 4.5 g (18.7 mmol) of the compound 25, and the mixture is reacted at the same temperature for 2 hours, and warmed up to −20° C. The solution is poured into ice-water and extracted with ether. The ether layer is washed with water, and dried over Na₂SO₄. The reaction mixture is filtered, and the filtrate is concentrated. The residue is subjected to column chromatography of silica gel eluting with methanol/toluene. The eluent is concentrated to prepare 1.14 g (Yield: 18.2%) of the compound 26 (E) as crystals. mp. 143°–144° C.

IRν (Nujol): 1603, 1498, 1222 cm⁻¹.

¹HNMR (CDCl₃)δ: 2.66 (s, 3H, CH₃); 3.46 (s, 3H, CH₃); 6.60 (s, 1H); 6.90–7.60 (m, 8H).

Further eluting with 5% methanol-toluene to prepare 1.86 g (Yield: 29.7%) of the compound 27 (Z) as crystals. mp. 175°–177° C.

IRν (Nujol): 1603, 1499, 1220 cm⁻¹.

¹HNMR (CDCl₃)δ: 2.14 (s, 3H, —CH₃); 3.76 (s, 3H, CH₃); 6.19 (s, 1H); 7.10–7.40 (m, 8H).

(3) The compound 26 (E) 1 g (3 mmol) obtained above is dissolved in 20 ml of carbon tetrachloride, mixed with 1.06 g (6 mmol) of N-bromosuccinimide and 100 mg (0.6 mmol) of α,α'-azobis-isobutylnitrile and refluxed for 1 hour. After cooling, the reaction mixture is filtered, and the filtrate is extracted with aqueous NaHCO₃. The organic layer is washed with water, dried over Na₂SO₄ and concentrated. The residue is subjected to column chromatography of silica gel eluting with 1%-methanol/methylene chloride. The obtained purificated product is washed with isopropyl ether to obtain the bromo compound. To a solution of sodium ethoxide, which is prepared by the reaction with 61 mg of sodium and 5.5 ml of absolute ethanol, is added 237 mg (2.66 mmol) of 2-nitropropane. The reaction mixture is stirred at room temperature for 10 minutes, and added bromo compound 550 mg (1.33 mmol) obtained above is added thereto. The reaction mixture is reacted at room temperature for 1 hour, mixed with ice-water and 10%-NaOH, and extracted with methylene chloride. The methylene chloride layer is washed with water, dried over Na₂SO₄, and filtered. The filatrate is concentrated, and the residue is recrystallized from ethyl acetate/isopropyl ether to prepare 400 mg (Yield: 86%) of the compound (II'-1) (E). mp. 201°–203° C.

IRν (Nujol): 1650 cm⁻¹.

¹HNMR (CDCl₃)δ: 3.93 (s, 3H); 6.80 (s, 1H); 7.10–7.65 (m, 8H); 9.57 (s, 1H).

The compound 27 (Z) is reacted in the same manner to prepare the compound (II'-2). mp. 205°–208° C.

IRν (Nujol): 1658 cm⁻¹.

¹HNMR (CDCl₃)δ: 3.99 (s, 3H); 6.80 (s, 1H); 7.00–7.65 (m, 8H); 9.58 (s, 1H).

EVALUATION OF BIOLOGICAL ACTIVITY

Experiment

The HMG-CoA Reductase Inhibitory Effect (1) Preparation of rat liver microsome

Sprague-Dawley rats, which had free access to ordinary diets containing 2% cholestyramine and water for 2 weeks, were used for the preparation of rat liver microsome, which was then purified according to the manner by Kuroda et al., Biochem. Biophys. Act, 486, 70 (1977). The microsomal fraction obtained by centrifugation at 105000×g was washed once with a buffered solution containing 15 mM nicotinamide and 2 mM magnesium chloride (in a 100 mM potassium phosphate buffer, pH 7.4). It was homogenized with a buffer containing nicotinamide and magnesium chloride at the same weight as the liver employed. The thus obtained homogenate was cooled down to and kept at −80° C.

(2) Measurement of the HMG-CoA reductase inhibitory activities.

The rat liver microsome (100 μl), which was preserved at −80° C., was fused at 0° C. and diluted with 0.7 ml of a cold potassium phosphate buffer (100 mM, pH 7.4). This was mixed with 0.8 ml of 50 mM EDTA (buffered with the aforementioned potassium phosphate buffer) and 0.4 ml of 100 mM dithiothreitol solution (buffered with the aforementioned potassium phosphate buffer), and the mixture was kept at 0° C. The microsome solution 1.675 ml was mixed with 670 μl of 25 mM NADPH (buffered with the aforementioned potassium phosphate buffer), and the solution was added to the solution of 0.5 mM [3-$^{14}$C]HMG-CoA (3 mCi/mmol). Potassium phosphate buffer of the test compound 5 μl is added to the mixture of microsome and HMG-CoA 45 μl, and the resulting mixture was incubated at 37° C. for 30 minutes and cooled. After termination of the reaction by addition of 10 μl of 2N-HCl, the mixture was incubated again at 37° C. for 15 minutes and then 30 μl of this mixture was applied to thin-layer chromatography of silica gel of 0.5 mm in thickness (Merck AG, Art 5744). The chromatograms were developed in toluene/acetone (1/1) and the sections, whose Rf value was between 0.45 to 0.6, were scraped. The obtained products were put into a vial containing 8 ml of scintillator to measure specific radio-activity with a scintillation counter. The results are shown in Table 2.

TABLE 2

| Test Compound | HMG-CoA reductase inhibitory activity IC$_{50}$(μM/l) |
|---|---|
| Ia-2 | 0.9 |
| Ia-5 | 0.11 |
| Ia-7 | 0.27 |
| Ia-9 | 0.032 |
| Ia-11 | 0.22 |
| Ia-12 | 0.74 |
| Ia-14 | 0.02 |
| Ia-15 | 0.063 |
| Ia'-1 | 0.09 |
| Ia'-2 | 0.09 |

What we claim is:

1. A compound represented by the formula:

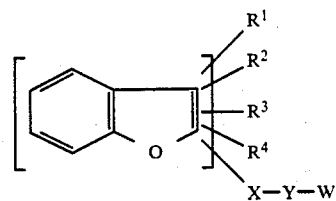

wherein $R^1$ and $R^2$ each is hydrogen, halogen or optionally substituted amino; $R^3$ and $R^4$ each is optionally substituted lower alkyl or optionally substituted phenyl; X-Y is —$CZ^7$=$CZ^1$— or —$CHZ^7$—$CHZ^2$—; W is

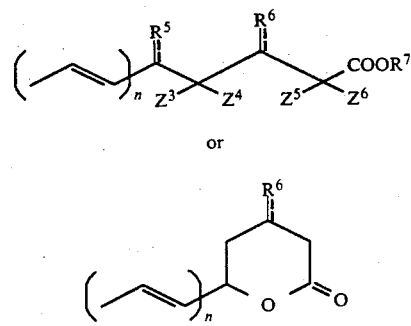

or wherein $R^5$ and $R^6$ each is hydroxy or oxo; $R^7$ is hydrogen, lower alkyl, quaternary ammonium, alkali metal or alkaline earth metal; $Z^1$, $Z^2$ and $Z^7$ each is hydrogen, optionally substituted phenyl, or optionally substituted tetrazole; $Z^3$, $Z^4$, $Z^5$ and $Z^6$ each is hydrogen or halogen; the dotted line represents the presence or absence of a double bond; and n is an integer of 0 or 1.

2. The compound claimed in claim 1, wherein said compound has an optically active form.

3. The HMG-CoA reductase inhibitor comprising the compound claimed in claim 1 as an active ingredient.

4. An intermediate compound represented by the formula:

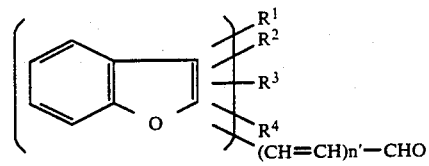

wherein $R^1$, $R^2$, $R^3$, and $R^4$ each has the same meaning as defined above; n' is an integer of 0 to 2; $R^1$, $R^2$, $R^3$, $R^4$, and (CH=CH)n'—CHO each may be attached to either benzene ring or furan ring.

* * * * *